(12) United States Patent
Kidishman et al.

(10) Patent No.: US 11,779,252 B2
(45) Date of Patent: Oct. 10, 2023

(54) RANDOM PINOUT CATHETER

(71) Applicant: Biosense Webster (Israel) Ltd., Yokneam (IL)

(72) Inventors: Eden Kidishman, Modiin (IL); Tamir Yellin, Yokneam Hamoshava (IL); Eliyahu Ravuna, Kiryat Ata (IL); Itamar Bustan, Zichron Ya'acov (IL); Assaf Govari, Haifa (IL); Dean Ponzi, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 352 days.

(21) Appl. No.: 17/204,504

(22) Filed: Mar. 17, 2021

(65) Prior Publication Data

US 2021/0244334 A1     Aug. 12, 2021

Related U.S. Application Data

(63) Continuation of application No. 15/722,846, filed on Oct. 2, 2017, now Pat. No. 10,959,635.

(51) Int. Cl.
*A61B 18/12*     (2006.01)
*A61B 5/287*     (2021.01)
(Continued)

(52) U.S. Cl.
CPC .............. *A61B 5/287* (2021.01); *A61B 5/333* (2021.01); *A61B 5/339* (2021.01); *A61B 5/6852* (2013.01);
(Continued)

(58) Field of Classification Search
CPC ............ A61B 18/1492; A61B 18/1233; A61B 2018/00988; A61B 2018/00172;
(Continued)

(56) References Cited

U.S. PATENT DOCUMENTS

| 4,385,272 A | 5/1983 | Whitehead |
| 5,766,133 A | 6/1998 | Faisandier |

(Continued)

FOREIGN PATENT DOCUMENTS

| JP | S61-176868 A | 8/1986 |
| JP | 2005-074104 A | 3/2005 |

(Continued)

OTHER PUBLICATIONS

International Search Report and Written Opinion dated Jan. 11, 2019 for PCT International Application No. PCT/US2018/052512.
(Continued)

*Primary Examiner* — Thomas A Giuliani
(74) *Attorney, Agent, or Firm* — Volpe Koenig

(57) ABSTRACT

A catheter is disclosed comprising: a connector including a plurality of first contacts and one or more second contacts; a shaft including a plurality of electrodes, each electrode being coupled to a different one of the plurality of first contacts; a memory coupled to at least one of the second contacts, wherein the memory is configured to: store a pinout map identifying an order in which the plurality of electrodes is coupled to the plurality of first contacts; and provide the pinout map to an external device via one or more of the second contacts after the connector is coupled to the external device.

8 Claims, 19 Drawing Sheets

(51) Int. Cl.
  *A61B 5/00* (2006.01)
  *A61M 39/10* (2006.01)
  *A61B 18/14* (2006.01)
  *A61B 5/333* (2021.01)
  *A61B 5/339* (2021.01)

(52) U.S. Cl.
  CPC .......... *A61B 5/743* (2013.01); *A61B 18/1492* (2013.01); *A61M 39/10* (2013.01); *A61B 2562/08* (2013.01); *A61B 2562/226* (2013.01); *A61M 2039/1022* (2013.01)

(58) Field of Classification Search
  CPC ...... A61B 2018/00178; A61B 2562/08; A61B 2562/226; A61M 39/10; A61M 2039/1022
  USPC ........... 606/32, 34, 41; 607/98, 99, 115, 116
  See application file for complete search history.

(56) References Cited

U.S. PATENT DOCUMENTS

| | | | |
|---|---|---|---|
| 6,298,255 | B1 | 10/2001 | Cordero et al. |
| 6,488,530 | B2 | 12/2002 | Ohlsson |
| 6,796,980 | B2 | 9/2004 | Hall |
| 6,823,208 | B2 * | 11/2004 | Ohlsson ................. A61B 5/304 600/509 |
| 7,713,194 | B2 | 5/2010 | Zdeblick |
| 8,109,883 | B2 | 2/2012 | Meyer et al. |
| 9,522,048 | B1 | 12/2016 | Schmit et al. |
| 9,532,725 | B2 | 1/2017 | Laughner et al. |
| 10,470,682 | B2 | 11/2019 | Deno et al. |
| 10,959,635 | B2 * | 3/2021 | Kidishman ........ A61B 18/1492 |
| 2001/0021799 | A1 | 9/2001 | Ohlsson |
| 2005/0182466 | A1 | 8/2005 | Mahajan |
| 2010/0152726 | A1 | 6/2010 | Cadouri et al. |
| 2015/0229088 | A1 * | 8/2015 | Johnson ............. H01R 43/0249 901/42 |
| 2015/0235057 | A1 | 8/2015 | Simmons |
| 2016/0136445 | A1 | 5/2016 | Blumstein et al. |
| 2016/0283612 | A1 * | 9/2016 | Toyama ................. G06F 30/00 |
| 2016/0283840 | A1 | 9/2016 | Amir et al. |

FOREIGN PATENT DOCUMENTS

| | | |
|---|---|---|
| JP | 2016-059772 A | 4/2016 |
| WO | 99/22799 A1 | 5/1999 |
| WO | 2016/089781 A1 | 6/2016 |

OTHER PUBLICATIONS

Chinese Office Action dated Nov. 24, 2022 for Chinese Patent Application No. 201880064551.0.
Japanese Office Action dated Aug. 2, 2022 for Japanese Patent Application No. 2020-539679.
International Preliminary Report on Patentability dated Apr. 7, 2020 for PCT International Application No. PCT/US2018/052512.

* cited by examiner

700

| Contact | Electrode |
|---|---|
| Contact[1] | Electrode[2] |
| Contact[2] | Electrode[8] |
| Contact[3] | Electrode[6] |
| Contact[4] | Electrode[7] |
| Contact[5] | Electrode[4] |
| Contact[6] | Electrode[5] |
| Contact[7] | Electrode[10] |
| Contact[8] | Electrode[3] |
| Contact[9] | Electrode[1] |
| Contact[10] | Electrode[9] |

710 (each row)

1328

| Connector 1322 Contacts | Electrode |
|---|---|
| Contact[1]<br>(connected to contact[1] of input interface 1332) | Electrode[2] | ⟵1328a
| Contact[2]<br>(connected to contact[2] of input interface 1332) | Electrode[8] | ⟵1328a
| Contact[3]<br>(connected to contact[3] of input interface 1332) | Electrode[6] | ⟵1328a
| Contact[4]<br>(connected to contact[4] of input interface 1332) | Electrode[7] | ⟵1328a
| Contact[5]<br>(connected to contact[5] of input interface 1332) | Electrode[4] | ⟵1328a
| Contact[6]<br>(connected to contact[6] of input interface 1332) | Electrode[5] | ⟵1328a
| Contact[7]<br>(connected to contact[7] of input interface 1332) | Electrode[10] | ⟵1328a
| Contact[8]<br>(connected to contact[8] of input interface 1332) | Electrode[3] | ⟵1328a
| Contact[9]<br>(connected to contact[9] of input interface 1332) | Electrode[1] | ⟵1328a
| Contact[10]<br>(connected to contact[10] of input interface 1332) | Electrode[9] | ⟵1328a

1336

| Diagnostic Device 1310 Contacts | Electrode |
|---|---|
| Contact[1]<br>(connected to contact[1] of output interface 1333) | Electrode[8] | ⟵1336a
| Contact[2]<br>(connected to contact[2] of output interface 1333) | Electrode[2] | ⟵1336a
| Contact[3]<br>(connected to contact[3] of output interface 1333) | Electrode[6] | ⟵1336a
| Contact[4]<br>(connected to contact[4] of output interface 1333) | Electrode[10] | ⟵1336a
| Contact[5]<br>(connected to contact[5] of output interface 1333) | Electrode[5] | ⟵1336a
| Contact[6]<br>(connected to contact[6] of output interface 1333) | Electrode[4] | ⟵1336a
| Contact[7]<br>(connected to contact[7] of output interface 1333) | Electrode[7] | ⟵1336a
| Contact[8]<br>(connected to contact[8] of output interface 1333) | Electrode[3] | ⟵1336a
| Contact[9]<br>(connected to contact[9] of output interface 1333) | Electrode[9] | ⟵1336a
| Contact[10]<br>(connected to contact[10] of output interface 1333) | Electrode[1] | ⟵1336a

FIG. 13B

| Output Channel | Input Channel |
|---|---|
| Output Channel[2] (connected to contact[2] of output interface) | Input Channel[1] (connected to contact[1] of input interface 1332) |
| Output Channel[1] (connected to contact[1] of output interface) | Input Channel[2] (connected to contact[2] of input interface 1332) |
| Output Channel[3] (connected to contact[3] of output interface) | Input Channel[3] (connected to contact[3] of input interface 1332) |
| Output Channel[7] (connected to contact[7] of output interface) | Input Channel[4] (connected to contact[4] of input interface 1332) |
| Output Channel[6] (connected to contact[6] of output interface) | Input Channel[5] (connected to contact[5] of input interface 1332) |
| Output Channel[5] (connected to contact[5] of output interface) | Input Channel[6] (connected to contact[6] of input interface 1332) |
| Output Channel[4] (connected to contact[4] of output interface) | Input Channel[7] (connected to contact[7] of input interface 1332) |
| Output Channel[8] (connected to contact[8] of output interface) | Input Channel[8] (connected to contact[8] of input interface 1332) |
| Output Channel[10] (connected to contact[10] of output interface) | Input Channel[9] (connected to contact[9] of input interface 1332) |
| Output Channel[9] (connected to contact[9] of output interface) | Input Channel[10] (connected to contact[10] of input interface 1332) |

FIG. 13C

| Switch 1531 Input Channels | Electrodes |
|---|---|
| Input_Channel[1] | Electrode[2] |
| Input_Channel[2] | Electrode[8] |
| Input_Channel[3] | Electrode[6] |
| Input_Channel[4] | Electrode[7] |
| Input_Channel[5] | Electrode[4] |
| Input_Channel[6] | Electrode[5] |
| Input_Channel[7] | Electrode[10] |
| Input_Channel[8] | Electrode[3] |
| Input_Channel[9] | Electrode[1] |
| Input_Channel[10] | Electrode[9] |

1526

1526a (each row)

| Diagnostic Device 1510 Contacts | Electrode |
|---|---|
| Contact[1] (connected to contact channel[1] of connector 1523 | Electrode[8] |
| Contact[2] (connected to contact channel[2] of connector 1523 | Electrode[2] |
| Contact[3] (connected to contact channel[3] of connector 1523 | Electrode[6] |
| Contact[4] (connected to contact channel[4] of connector 1523 | Electrode[10] |
| Contact[5] (connected to contact channel[5] of connector 1523 | Electrode[5] |
| Contact[6] (connected to contact channel[6] of connector 1523 | Electrode[4] |
| Contact[7] (connected to contact channel[7] of connector 1523 | Electrode[7] |
| Contact[8] (connected to contact channel[8] of connector 1523 | Electrode[3] |
| Contact[9] (connected to contact channel[9] of connector 1523 | Electrode[9] |
| Contact[10] (connected to contact channel[10] of connector 1523 | Electrode[1] |

1527

1527a (each row)

FIG. 15B

RANDOM PINOUT CATHETER

CROSS REFERENCE TO RELATED APPLICATIONS

This application is a continuation of U.S. patent application Ser. No. 15/722,846, filed Oct. 2, 2017, now U.S. Pat. No. 10, 959, 635, which is incorporated by reference as if fully set forth.

SUMMARY

The present disclosure relates to medical devices in general, and more particularly, to a random pinout catheter.

Cardiac catheterization is a medical procedure used to diagnose and treat various cardiovascular conditions. During cardiac catheterization, a catheter is inserted into a patient's heart through the patient's veins or arteries. The catheter may be a thin tube having electrodes on one end and a handle and a connector on the other. The electrodes may be connected to different pins in the connector via a set of wires that extend along the tube. The connector may be plugged into a diagnostic device which processes signals received from the electrodes to provide useful diagnostic information to doctors and other medical professionals.

When a catheter is manufactured, connecting the wires to the connector can be very labor intensive. The wires can be so thin (e.g., 80 microns) that they cannot be color-coded in a way that makes it possible for factory workers to distinguish the wires from one another. This requires factory workers to use a continuity tool (e.g., a multimeter) to identify the electrode connected to each wire in order to determine the connector pin which the wire belongs to. Doing so adds approximately 1 hour to the manufacturing process, thereby resulting in an increased manufacturing cost.

Accordingly the need exists for new manufacturing techniques and catheter designs that simplify the manner in which catheter connectors are connected to the electrode wires.

The present disclosure addresses this need. According to aspects of the disclosure, a catheter is disclosed comprising: a connector including a plurality of first contacts and one or more second contacts; a shaft including a plurality of electrodes, each electrode being coupled to a different one of the plurality of first contacts; a memory coupled to at least one of the second contacts, wherein the memory is configured to: store a pinout map identifying an order in which the plurality of electrodes is coupled to the plurality of first contacts; and provide the pinout map to an external device via one or more of the second contacts after the connector is coupled to the external device.

According to aspects of the disclosure, a catheter is disclosed comprising: a switch including a plurality of input channels and a plurality of output channels; a connector including a plurality of contacts, each of the contacts being coupled to a different one of the output channels of the switch; a shaft including a plurality of electrodes, each electrode being coupled to a different one of the plurality of input channels of the switch; a memory configured to store a first pinout map identifying a first order in which the plurality of electrodes is coupled to the plurality of input channels of the switch; and a processor coupled to the memory and the switch, the processor being configured to transition the switch from a first state to a second state based on the first pinout map, the second state being one in which the switch is arranged to couple the plurality electrodes to the plurality of contacts in a second order that is compatible with at least one external device.

According to aspects of the disclosure, a method for configuring a catheter is disclosed, comprising: inserting a shaft of the catheter in a deployment location, the shaft including a plurality of electrodes disposed in a linear order on the shaft; detecting a plurality of signal changes that occur during the insertion of the catheter in the deployment location, each signal change being a change in a value of a different signal that is received at a respective one of a plurality of channels from one of the electrodes; and generating a pinout map associating each of the electrodes with a different one of the plurality of channels based on a temporal order in which the signal changes are detected.

BRIEF DESCRIPTION OF THE DRAWINGS

The drawings described below are for illustration purposes only. The drawings are not intended to limit the scope of the present disclosure. Like reference characters shown in the figures designate the same parts in the various embodiments.

FIG. 13B is a diagram of an example of a plurality of data structures used by the system of FIG. 13A, according to aspects of the disclosure;

FIG. 13C is a diagram of an example of a data structure used by the system of FIG. 13A, according to aspects of the disclosure;

FIG. 15B is a diagram of an example of a plurality of data structures used by the system of FIG. 15A, according to aspects of the disclosure;

DETAILED DESCRIPTION

Figure 1:
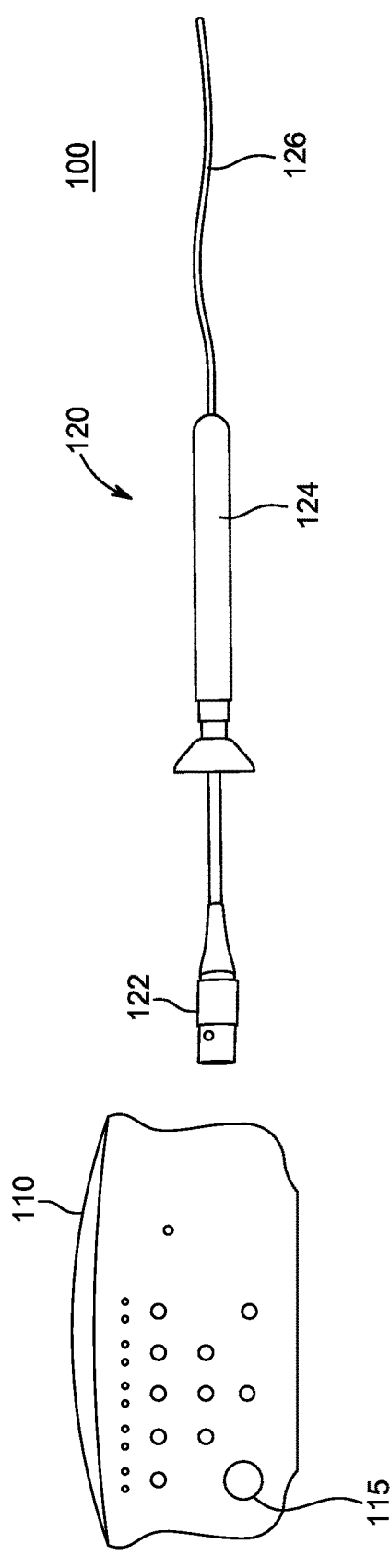
FIG. 1 is a diagram of an example of a system including a catheter, according to aspects of the disclosure.

A diagnostic catheter may include a shaft having multiple electrodes disposed on one end of the shaft. The electrodes may be connected to wires that extend along the shaft and come out of the other end of the shaft to be coupled to a connector. When a diagnostic catheter is manufactured, plant workers need to determine which wire belongs to which electrode, so that they can solder the wires to the correct contacts of the connector. However, this may be a time consuming process. For example, wiring a catheter that includes 22 electrodes may add 1 hour to the time it takes to manufacture the catheter. This time is largely spent by workers to trace the specific wire each electrode is connected to and solder that wire to a connector that has been designated for that electrode.

According to aspects of the disclosure, an improved catheter is disclosed that can be manufactured in a shorter time than catheters in the prior art. In the improved catheter, different electrodes are connected at random to the contacts of a connector (or another component), while a pinout map indicating the order in which the electrodes are connected is stored in a memory device integrated into the catheter. Connecting the electrodes at random may reduce the time it takes to manufacture the catheter by 30 minutes resulting in an increased manufacturing yield. The reduction in time is largely due to workers not having to identify the specific wire each electrode is connected to before coupling that wire to a given connector contact (or another component).

According to aspects of the disclosure, an improved catheter is disclosed that includes a memory device (e.g., an EEPROM) integrated therewith and a shaft whose electrodes are connected at random to different contacts of the catheter's connector. Because the electrodes are connected at random to the connector contacts, the catheter cannot be used without a pinout map that is stored in the memory device to identify the contact each electrode is connected to. Accordingly, when the catheter is connected to an external device, the pinout map is retrieved by the external device and used to interpret the signals received from different electrodes of the catheter.

According to another aspect of the disclosure, a configuration device is disclosed for generating the pinout map of the improved catheter. The configuration device may be used during the manufacturing of the improved catheter and it may include a first receptacle and a second receptacle. The first receptacle may be arranged to receive the shaft of the improved catheter on which electrodes are mounted. The second receptacle may be arranged to receive the connector of the catheter. When the shaft of the catheter is inserted into the first receptacle and the connector of the catheter is inserted into the second receptacle, the configuration device determines the connector contact each electrode is connected to, generates a pinout map identifying the connector contact each electrode is connected to, and stores the pinout map in the memory device that is integrated into the catheter.

According to aspects of the disclosure, an interface adapter is disclosed for use with the improved catheter. The interface adapter is designed to be interposed between the improved catheter and a diagnostic device. In operation, the interface adapter may switch the signals received from the electrodes of the catheter to an order that is supported by the diagnostic device, and feed the switched signals to the diagnostic device. The switching may be performed based on the pinout map that is stored in the improved catheter. The interface device may permit the improved catheter to be used with legacy diagnostic devices which lack the capability to retrieve and interpret the pinout map of the catheter on their own.

According to aspects of the disclosure, a method is disclosed for dynamically associating signals received from the improved catheter with specific electrodes in the catheter while the catheter is being inserted into a patient's body. The method may be performed when the electrodes of the improved catheter are connected at random to the catheter's connector, so and it is unknown which signal is received from which electrode. An advantage of this method is that it does not require a memory device or other extra hardware to be integrated into the catheter in order for the catheter to be usable.

More particularly, according to the method, when a catheter is inserted into patient's body it may be contained in a sheath. The sheath may be a plastic tube of larger diameter than the catheter which is used to limit pain and increase accuracy. The catheter may stay in the sheath until the location is reached where the catheter needs to be deployed (e.g., the patient's heart). At this point, the end of the catheter which contains electrodes may be slid out of the sheath to enter the location. Because the electrodes are arranged in a line on the end of the catheter, they leave the sheath one after another. When each electrode leaves the sheath, the signal generated by the electrode changes as a result of the electrode coming in contact with the patient's tissues. By monitoring the order in which signal changes occur, the electrode which is the source of each signal may be identified. For example, the signal that changes first may be associated with the first electrode on the catheter (counting from the tip), while the signal that changes third may be associated with the third electrode on the catheter (counting from the tip).

Examples of various catheters and catheter systems will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. It will be understood that these terms are intended to encompass different orientations of the element in addition to any orientation depicted in the figures.

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

FIG. 1 is a diagram of an example of a system 100, according to aspects of the disclosure. The system includes a diagnostic device 110 and a catheter 120 that is arranged to connect to the diagnostic device via a connector 122. The diagnostic device 110 may be an ECG monitor and/or any other suitable device that is arranged to receive and interpret signals from the catheter 120. The catheter 120 may be any suitable type of catheter, such as a cardiac catheter for example. The catheter 120 may include a handle 124 and a shaft 126 having a plurality of electrodes in it. In operation, the handle 124 may be used to thread the shaft 126 through an artery or vein of a patient to a destination which is desired to be examined with the catheter, such as a heart chamber. When the destination is reached, each of the electrodes in the catheter may provide a different signal to the electronic device which is then used to diagnose the patient. The signals may be delivered to the diagnostic device via the connector 122.

In order for the diagnostic device 110 and the catheter 120 to interoperate, they must both comply with the same interface standard. As used throughout the disclosure, the term "interface standard" is defined as a specification of a mapping between different electrodes on the catheter and different contacts (e.g., pins) on the connector. Put differently, the connector standard may specify the order in which different electrodes are connected to different contacts of a connection interface (e.g., a connector, a receptacle arranged to receive a connector, etc.) For example, an interface standard for a three-pin connector may specify that pin[1] carries a signal generated by electrode[1], pin [2] carries a signal generated by electrode[2], and pin[3] carries a signal generated by electrode[3]. As can readily be appreciated, compliance with the same interface standard is essential for successful interoperability between the diagnostic device 110 and the catheter 120. In the example of FIG. 1, the catheter 120 complies with an interface standard supported by the diagnostic device 110, which permits the catheter 120 to be plugged directly into the receptacle 115 of the diagnostic device 110.

Figure 2:
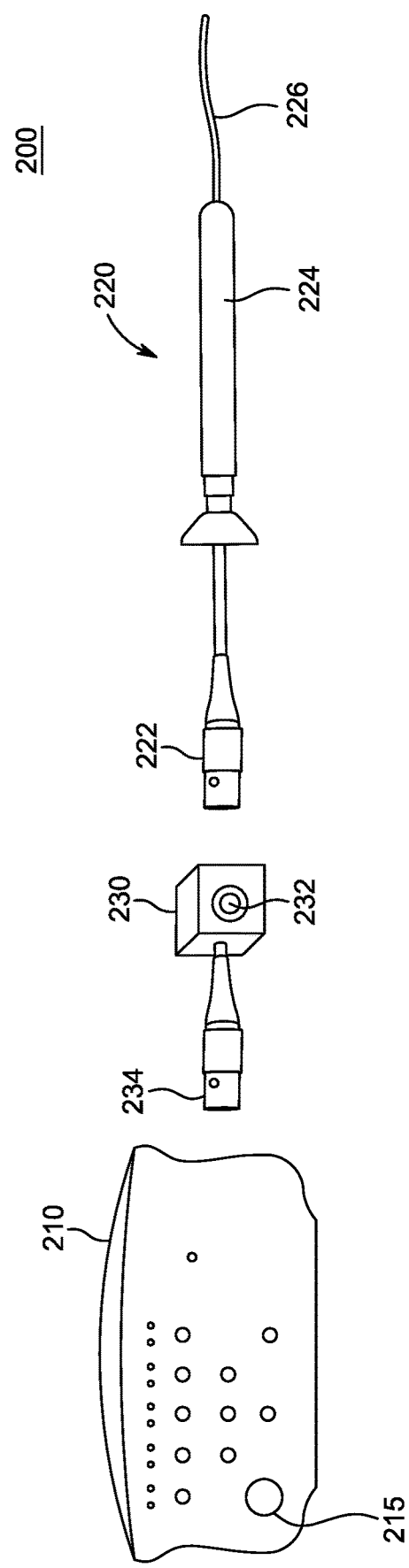
FIG. 2 is a diagram of an example of a system including a catheter, according to aspects of the disclosure.

FIG. 2 is a diagram of an example of a system 200, according to aspects of the disclosure. The system 200 includes a diagnostic device 210 and a catheter 220. The catheter 220 includes a connector 222, a handle 224, and a shaft 226. The catheter 220, in this example, does not comply with any interface standard supported by the diagnostic device 210. Accordingly, the catheter 220 cannot be plugged directly into the receptacle 215 of the diagnostic device and requires the use of an interface adapter 230.

The interface adapter 230 includes an input interface 232 and an output interface 234. The input interface 232 is arranged to receive the connector 222 of the catheter 220 and the output interface 234 is arranged to be plugged into the receptacle 215 of the diagnostic device 210. When the diagnostic device 210, the catheter 220, and the interface adapter 230 are connected in this way, the interface adapter 230 adapts the signals received from the catheter 220 to the interface standard supported by the diagnostic device 210 to make the catheter 220 and the diagnostic device 210 mutually compatible.

Figure 3:
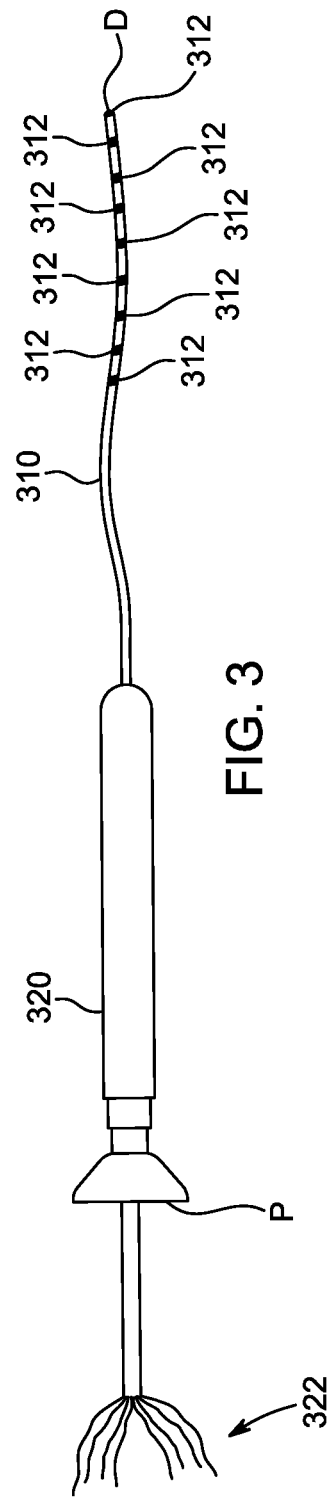
FIG. 3 is a diagram of an example of a catheter assembly, according to aspects of the disclosure.

FIG. 3 is a diagram of an assembly 300 including a catheter shaft 310 and a catheter handle 320, according to aspects of the disclosure. Electrodes 312 are arranged in sequence near the distal end D of the shaft 310, as shown. Each of the electrodes 312 is connected to a different electrode wire 322 that extends through the shaft and exits the assembly 300 through the proximal end P of the handle. Although not shown, built in the handle may be a memory device for storing a pinout map. In addition, in some implementations, built in the handle may be a controller, a switch, and/or any other suitable electronic component.

Figure 4:
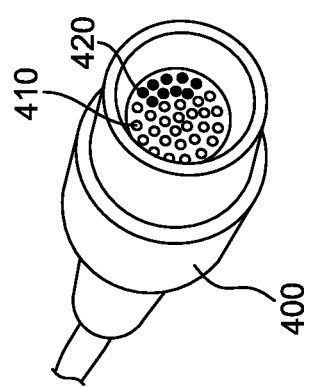
FIG. 4 is a diagram of an example of a connector, according to aspects of the disclosure.

FIG. 4 is a diagram of an example of a connector 400 that is designed to be connected to the assembly 300. The connector 400 includes a plurality of first contacts 410 and one or more second contacts 420. Each of the first contacts 410 may be connected to a different electrode wire 322 while any of the second contacts may be connected to at least one of a memory device that is built in the handle 320. Additionally or alternatively, in some implementations, one or more of the second contacts may be connected to a controller that is built-in the catheter, a communications interface (e.g., a serial interface) that is built in the handle 320, etc.

When the connector 400 is coupled to the assembly 300 to produce a finished catheter, the electrode wires 322 need to be soldered to the first contacts 410 of the connector 400. However, finding which wire comes from which pin, in order to solder it to the correct contact, may be a time consuming process. The electrode wires 322 may be very thin (e.g., 80 microns or 40-AWG) which makes it difficult to color code them in a way that makes it possible for plant workers to distinguish the wires from one another. This necessitates plant works to use a continuity tool to identify the electrode 312 each wire is connected to in order to determine the correct first contact 410 for the wire. In some instances, connecting the electrode wires 322 to the first contacts 410 may take close to an hour, thereby resulting in increased manufacturing costs.

Figure 5:
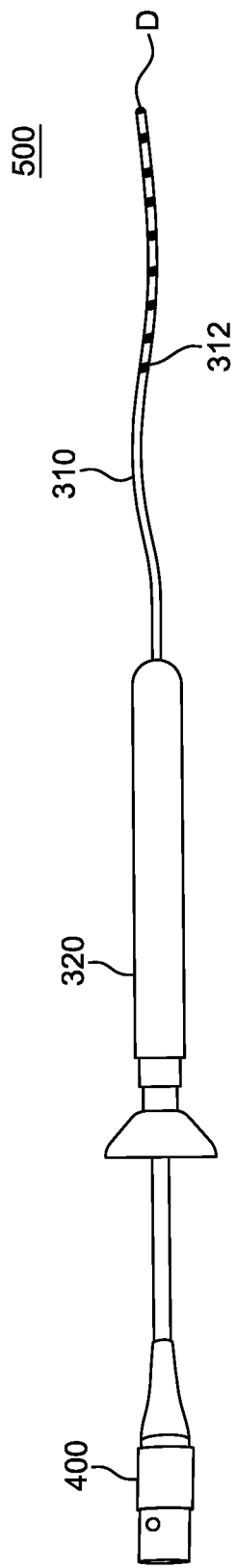
FIG. 5 is a diagram of an example of a catheter including the catheter assembly of FIG. 3 and the connector of FIG. 4, according to aspects of the disclosure.

FIG. 5 is a diagram of an example of a catheter 500 that is produced in accordance with an improved process for manufacturing catheters. According to the process, each of the electrode wires 322 is connected to a different contact 410 at random to form the catheter 500. Afterwards, the catheter 500 is programmed using a configuration device 600 (shown in FIG. 6) to store a pinout map that identifies the respective electrode 312 that is connected to each contact 410. The pinout map may be stored by the configuration device 600 into a memory device disposed in the handle 320 of the catheter 500 and subsequently used when the catheter 500 is connected to a particular diagnostic device. Notably, when a batch of catheters is manufactured using this process, the order in which the catheter electrodes are connected to the contacts of the catheter connector may vary across the batch. In this regard, the pinout map compensates for this variation and ensures normal operation of the catheters in the batch.

In some aspects, connecting the electrodes at random to the contacts 410 of the connector 400 (or another element) may have several structural implications with respect to the catheter 500. First, connecting the electrodes at random may result in them being connected in a non-standard order to the connector 400 (or another element). For example, a non-standard-order may be an order that does not comply with any particular interface standard that might be supported by a diagnostic device intended to utilize the catheter. As another example, a non-standard order may be an order that does not comply with any particular industry-wide and/or manufacturer-specific interface standard. As noted above, any interface standard specifies the order in which the signals from specific electrodes need to be placed on the input channels of a diagnostic device. Unless the signals are put in that order, the device may not know the identity of this signal and be able to operate correctly. Thus, a catheter whose electrodes are connected at random to the contacts of its connector (and/or to another component, such as a switch) may be unable to function properly unless the catheter is provided with additional features. Second, connecting the electrodes at random may require the provision of a memory device on the catheter that stores a pinout map for the catheter. As noted above, the pinout map may identify the contact each electrode is connected to, thus permitting the catheter to be used in conjunction with standard medical equipment.

Figure 6:
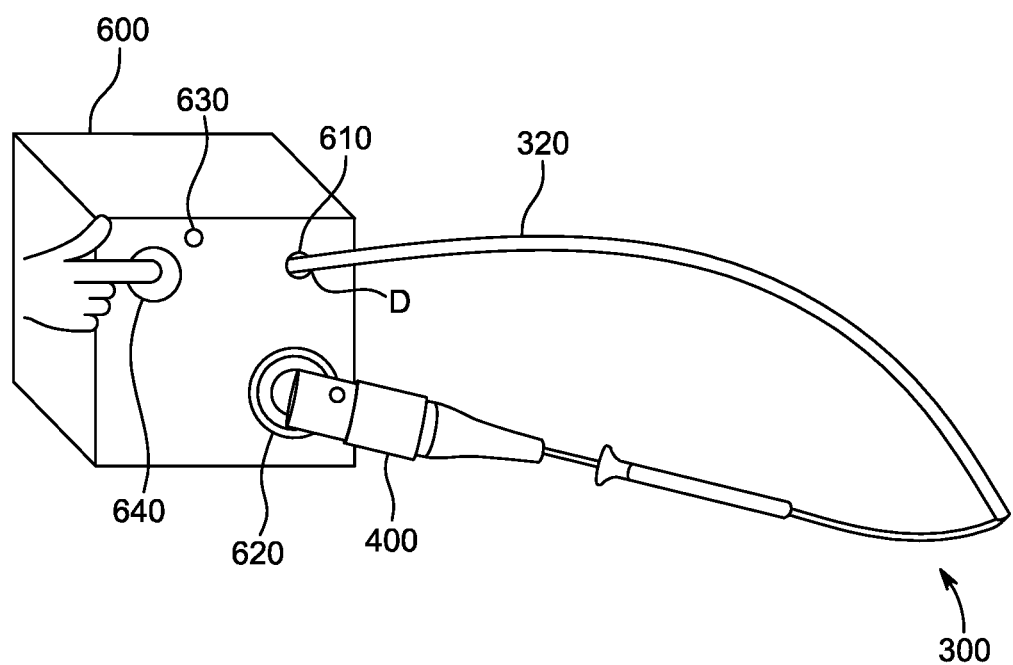
FIG. 6 is a diagram illustrating an example of a process for programming the catheter of FIG. 5 by using a configuration device, according to aspects of the disclosure.

FIG. 6 is a diagram illustrating a process for programming the catheter 500 by using a configuration device 600. In accordance with the process, the distal end D of the shaft 310 is inserted into a receptacle 610 whereas the connector 400 is inserted into a receptacle 620. Afterwards, the configuration device performs a sequence of tests on the catheter to determine the connectivity between the electrodes 312 and the contacts 410. When the sequence of tests is completed, the light emitting diode (LED) 630 is turned green to inform the plant worker operating the configuration device 600 that the sequence of tests is completed. Afterwards, when the button 640 is pressed, a pinout map is generated and stored in a memory device that is integrated in the catheter 500 (e.g., in the handle of the catheter, etc.)

Figures 7, 8:
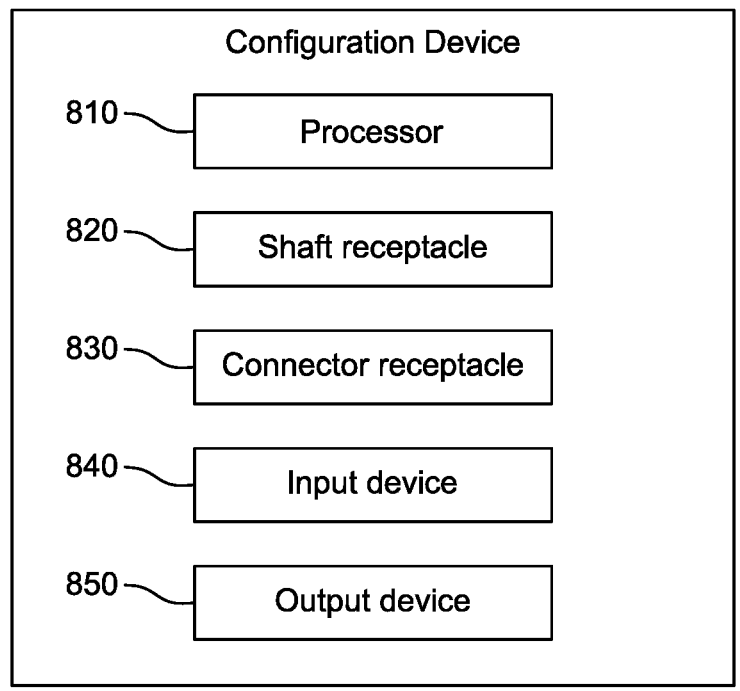
FIG. 7 is a diagram of an example of a pinout map that is generated as a result of executing the process of FIG. 6, according to aspects of the disclosure.
FIG. 8 is a diagram of an example of a configuration device, according to aspects of the disclosure.

FIG. 7 is a diagram of an example of a pinout map 700 that is generated by the configuration device 600. As illustrated, the pinout map 700 includes a plurality of mappings 710. Each mapping 710 is associated with a different one of the electrodes 312. Furthermore, each mapping 710 identifies a contact 410 on the connector 400 that is connected to that mapping's respective electrode. Although in the present example, the pinout map 700 is represented in a tabular format, it will be understood the pinout map 700 may be any suitable type of data structure capable of identifying the respective contact 410 that is connected to each one of the electrodes 312. Furthermore, although in the example of FIG. 7, each mapping 710 is represented as a table row, it will be understood that any of the mappings 710 may include a number, a letter, a special character, an alphanumerical string, and/or any other suitable type of data structure that is capable of identifying an electrode and a contact to which the electrode is connected.

FIG. 8 is a schematic diagram of a configuration device 800 that can be used to program the catheter 500. The configuration device 800 may be the same or similar to the configuration device 600. The configuration device 800 may include a processor 810, a shaft receptacle 820, a connector receptacle 830, an input device 840, and an output device 850. The processor 810 may include any suitable type of processing circuitry, such as one or more of a general purpose processor (e.g., an ARM-based processor), an application-specific integrated circuit (ASIC), a field-programmable gate array (FPGA), a complex programmable logic device (CPLD), or a microcontroller, for example. The shaft receptacle 820 may be any suitable type of receptacle that is arranged to receive the distal end D of the catheter shaft 310. The connector receptacle 830 may be any suitable type of connector that is arranged to be coupled to the connector 400. The input device 840 may include one or more of a button, a microphone, a keyboard, a touch screen, and/or any other suitable type of input device. The output device 850 may include one or more of a display, a speaker, a printer and/or any other suitable type of output device.

Figure 9:
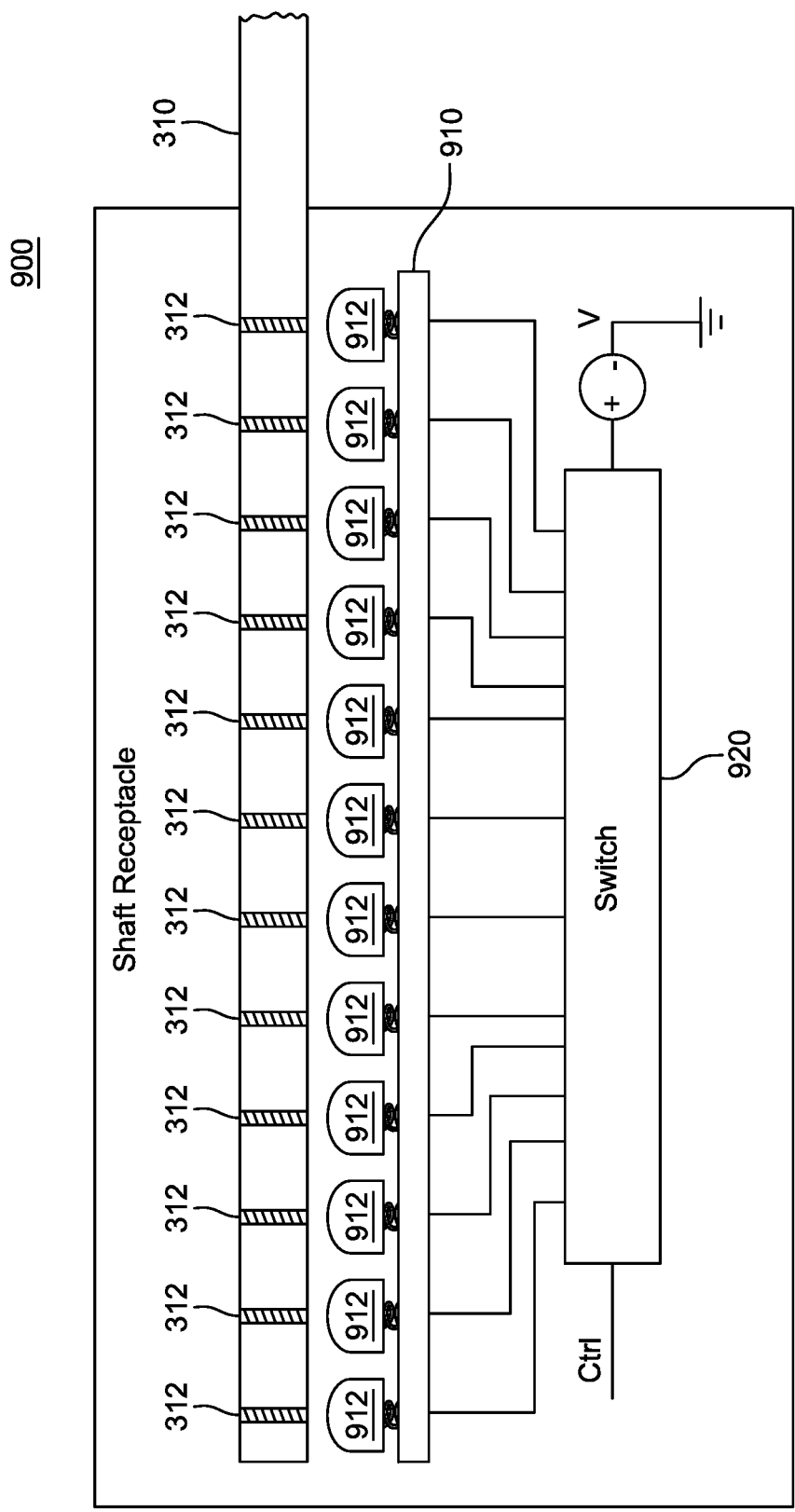
FIG. 9 is a diagram of an example of a shaft receptacle that can be integrated into the configuration device of FIG. 8, according to aspects of the disclosure.

FIG. 9 is a schematic diagram illustrating an example of the shaft receptacle 900, according to aspects of the disclosure. In accordance with this example, the shaft receptacle 900 includes a contact comb 910 having a plurality of spring-loaded contacts 912. The spring-loaded contacts 912 are arranged to come in contact with the electrodes 312 when the shaft 310 is inserted into the shaft receptacle 900, as shown. A switch 920 is configured to route a voltage signal V to one of the contacts 912 that is selected by the processor 810 via the control signal CTRL, which is at least in part generated by the processor 810. For example, when a first control signal is supplied to the switch 920 by the processor 810, the switch 920 may route the signal V to a first contact 912. As another example, when a second signal is supplied to switch 920 by the processor 810, the switch 920 may route the signal V to a second contact 912. As yet another example, when a third signal is supplied to switch 920 by the processor 810, the switch 920 may route the signal V to a third contact 912. In this regard, by using the switch 920, the processor 810 may apply a signal to each of the electrodes 312, one-by-one, to identify the electrode wire 322 that is connected to that electrode.

Figure 10:
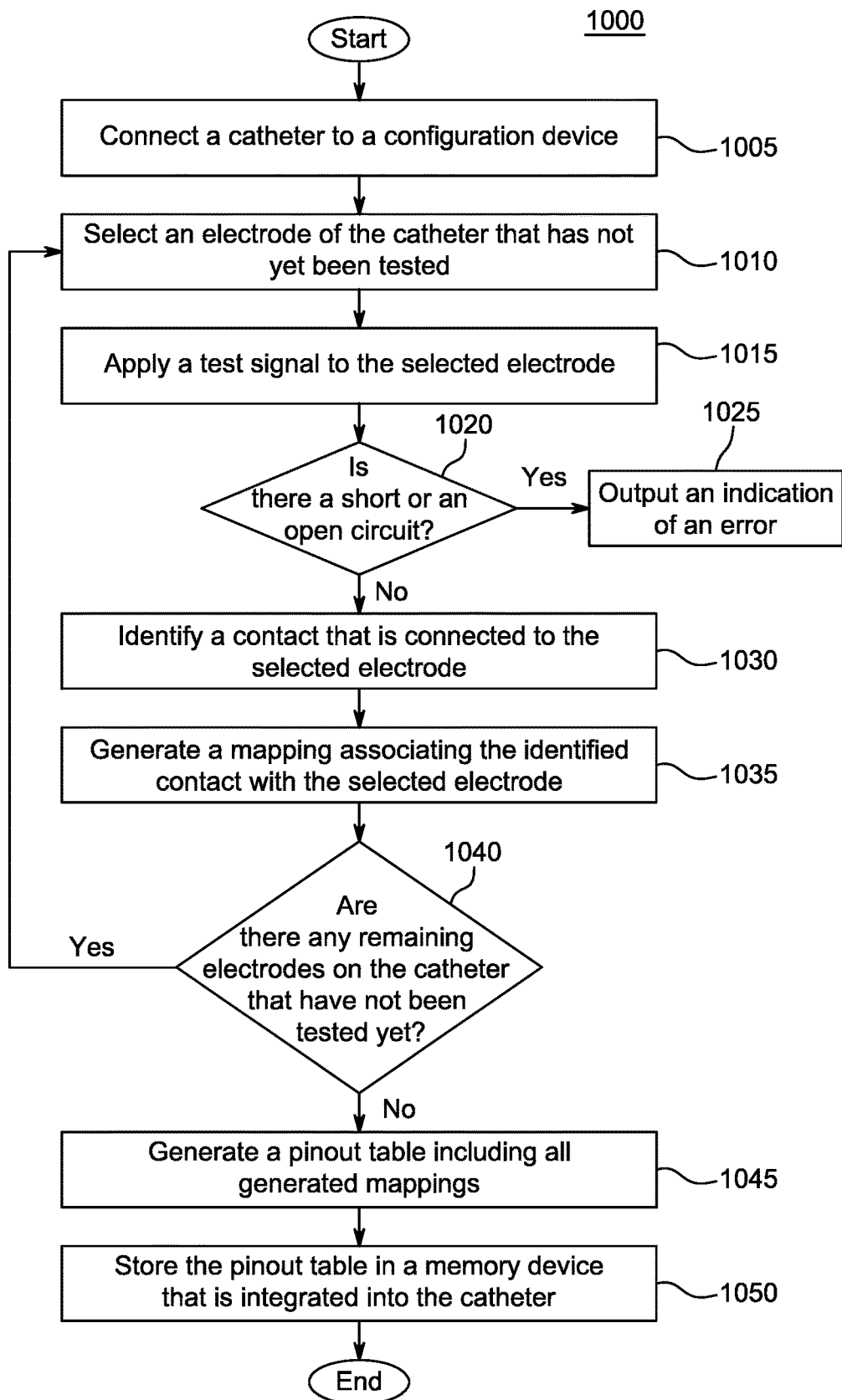
FIG. 10 is a flowchart of an example of a process for using the shaft receptacle of FIG. 9 to configure the catheter of FIG. 5, according to aspects of the disclosure.

FIG. 10 is a flowchart of an example of a process 1000 for generating a pinout map for the catheter 500 by using the shaft receptacle 900. The process may be performed by any suitable configuration device, such as one of the configuration devices 600 and 800, in which the shaft receptacle 900 is deployed.

At step 1005, the catheter 500 is connected to a configuration device by inserting the shaft 310 into the shaft receptacle 900 and plugging the connector 400 of the catheter 500 in a connector receptacle that is present in the configuration device.

At step 1010, an electrode 312 of the catheter 500 that has not been yet tested is selected. At step 1015, a test signal is applied to the untested electrode. The signal may be any suitable type of signal, such as a voltage signal or a current signal for example.

At step 1020 an error check is performed to determine if the wire 322 that is connected to the selected electrode is either severed and/or shorted with another wire. Performing the error check may include detecting whether the test signal is output on more than one of the contacts 410 of the connector 400. Additionally or alternatively, performing the error check may include detecting whether the applied signal is not output on any of the contacts 410.

At step 1025, in response to an error being detected, an indication of the error is output via an output device. For example, in instances in which the output device is an LED, the output device may emit red light. However, alternative implementations are possible in which outputting the error message includes outputting a sound, outputting a text message, outputting an image, etc. If no error is detected, the process proceeds to step 1030.

At step 1030, a respective contact 410 is identified that is connected to the selected electrode 312 via one of the wires 322. The respective contact 410 may be identified based on detecting that the test signal is output on the respective contact. For example, in instances in which the test signal is a voltage signal, the contact 410 may be selected by determining the voltage at each of the contacts 410 while the test signal is being applied to the selected electrode and identifying the contact 410 whose voltage is substantially the same to (or within a predetermined distance from) the voltage applied to the selected electrode.

At step 1035, a mapping 710 is generated that associates the selected electrode to the contact 410 it is connected to. As noted above, the mapping may include any suitable type of number, alphanumerical string, data primitive, and/or data structure indicating that the selected electrode is connected to the contact identified at step 1025.

At step 1040, a determination is made if there are any remaining electrodes 312 in the catheter 500 that have not yet been tested. If there are, steps 1010-1035 are repeated for each of the remaining electrodes. Otherwise, the process proceeds to 1045.

At step 1045, a pinout map is generated that includes each of the mappings generated during one or more prior iterations of steps 1010-1035. In some implementations, generating the pinout map may include encapsulating each mapping that is generated at step 1035 in the same data structure.

At step 1050, the generated pinout map is stored in a memory device that is integrated into the catheter 500.

Although in the present example, each electrode 312 is tested individually to determine the contact 410 which the electrode is connected to, alternative implementations are possible in which the process is reversed. In such instances, a signal may be applied to each of the contacts 410, one-by-one, to determine the respective electrode on which the signal is output. Similarly, an error check may be performed each time the signal is applied to a given contact to determine whether the contact is connected to more than one electrode 312 (due to a short) or not connected to any electrode 312 (due to a severed wire). Performing the error check may include at least one of determining whether the applied signal appears on multiple electrodes 312, or whether the applied signal does not appear on any of the electrodes 312.

Figure 11:
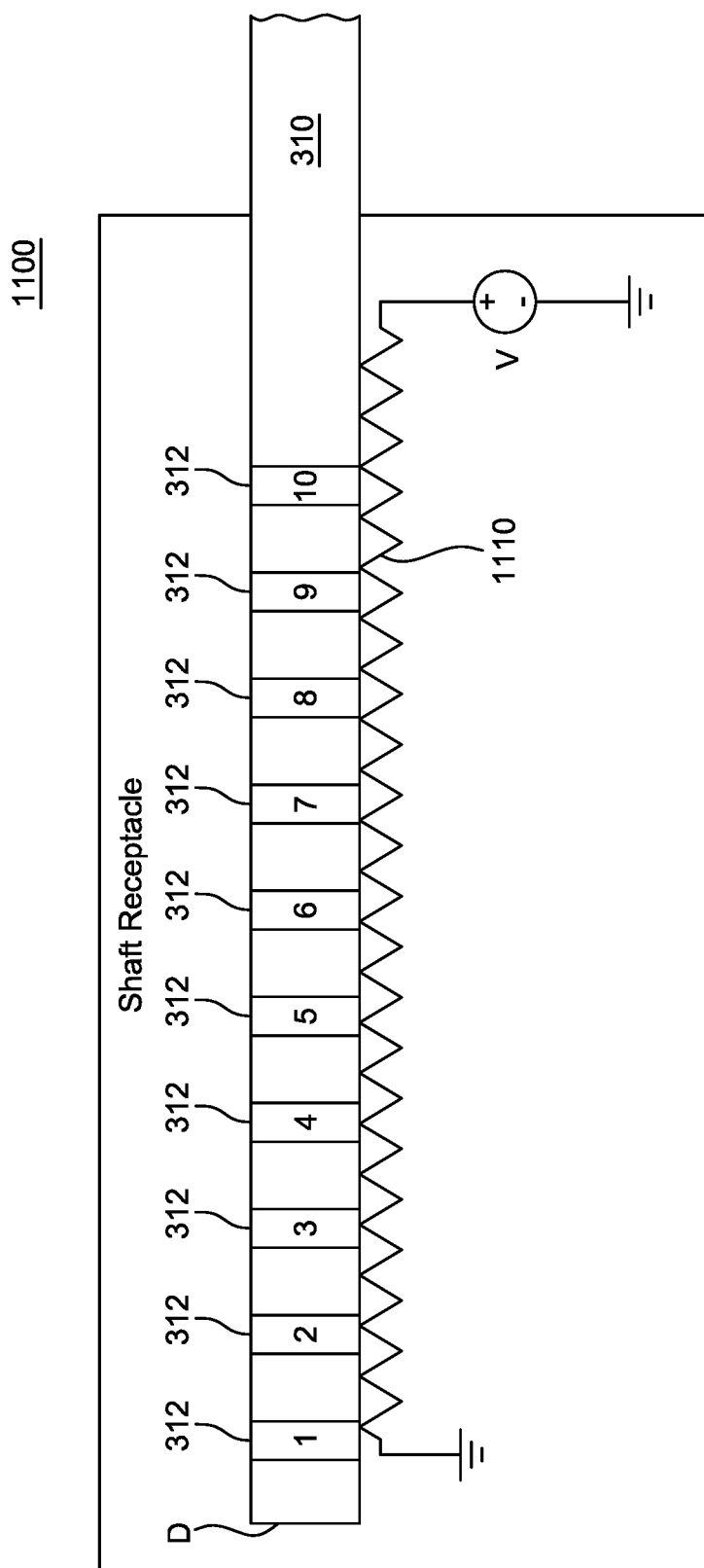
FIG. 11 is a diagram of an example of a shaft receptacle that can be integrated into the configuration device of FIG. 8, according to aspects of the disclosure.

FIG. 11 is a schematic diagram illustrating an example of a shaft receptacle 1100, according to aspects of the disclosure. In this example, the contact comb 910 is replaced with a resistive structure 1110, as shown. In some implementations, the resistive structure 1110 may be a long resistor made of a material such as Graphite, Polyaniline, or PEDOT. When the shaft 310 is inserted into the shaft receptacle 820, each electrode 312 may come in contact with the resistive structure 1110 at a different location. As a result, the voltage applied to each electrode 312 may be proportional to the distance between the electrode and the end the end of the resistive structure 1110 at which the voltage is applied. Specifically, the highest voltage may be applied to the electrode 312 that is the closest to the end while the lowest voltage may be applied to the electrode that is the furthest away from the end. Although in the present example the resistive structure 1110 includes a single resistor, alternative implementations are possible in which multiple resistors are used. For instance, in some implementations, the resistive structure may be a series of resistors, such that when the shaft 310 is inserted into the receptacle 1100, each electrode 312 is coupled to a different junction between two neighboring resistors in the series via a receptacle contact that is installed at the junction.

Figure 12:
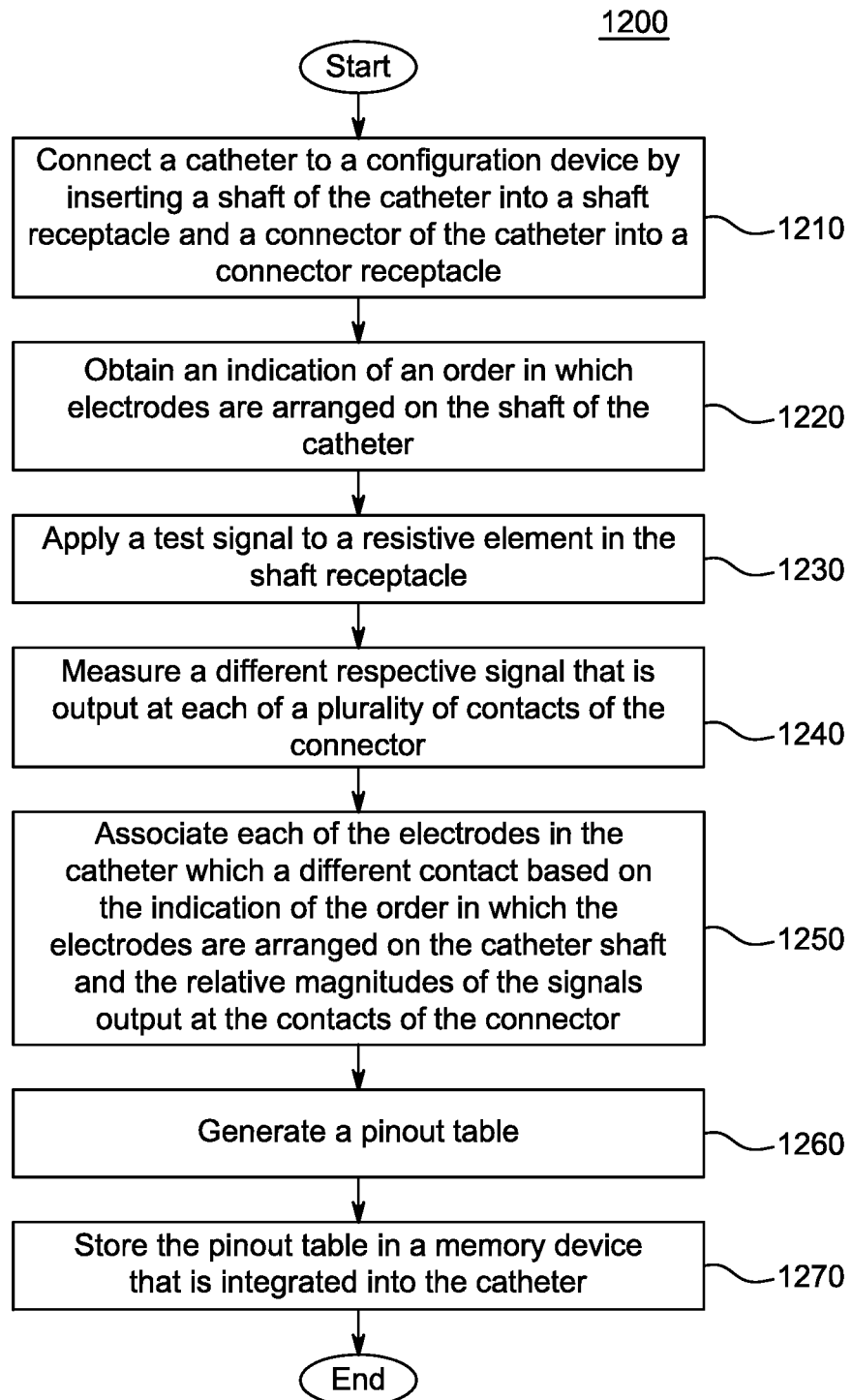
FIG. 12 is a flowchart of an example of a process for using the shaft receptacle of FIG. 11 to configure the catheter of FIG. 5, according to aspects of the disclosure.

FIG. 12 is a flowchart of an example a process 1200 for generating a pinout map for the catheter 500 by using the shaft receptacle 1100, according to aspects of the disclosure. The process 1200 may be performed by a configuration device, such as one of the configuration devices 600 and 800, in which the shaft receptacle 1100 is deployed.

At step 1210, the catheter 500 is connected to a configuration device by inserting the shaft 310 into the shaft receptacle 1100 and plugging the connector 400 of the catheter 500 in a connector receptacle that is present in the configuration device.

At step 1220, an indication is obtained of an order in which the electrodes 312 are arranged on the shaft 310 of the catheter 500. In some implementations, obtaining the indication may include retrieving the indication from a memory of the configuration device. Additionally or alternatively, obtaining the indication may include retrieving the indication from the catheter 500 or another device.

In some implementations, the indication may include a set of identifiers. As illustrated in FIG. 11, each identifier may include a different number. Furthermore, as illustrated in FIG. 11, each identifier may correspond to a different electrode. All electrodes having identifiers that are smaller than the identifier of a given electrode may be located closer to the distal end of the shaft 310 than the given electrode. Similarly, all electrodes having identifiers that are larger than the given electrode may be located further away from the distal end D of the shaft 310 than the given electrode. Stated succinctly, in some implementations, the location of a given electrode 312 on the shaft 310 may be specified implicitly or explicitly in the identifier used to reference the electrode.

Additionally or alternatively, in some implementations, the indication may include an ordered list of electrode identifiers. Each identifier in the list may correspond to a different electrode. The position of each identifier in the list may correspond to the position of the identifier's electrode 312 on the shaft 310. For instance, the closer a given electrode 312 is to the distal end D of the shaft 310, the closer the electrode's identifier may be to the beginning of the list.

At step 1230, a voltage is applied to the resistive structure 1110 that is part of the shaft receptacle 1100. At step 1240, the respective signal output at each of the contacts 410 is detected. More particularly, in some implementations, at steps 1230-1240, a voltage may be applied to the resistive element 1110, while the voltage at each of the contacts 410 is being measured. As can be readily appreciated, steps 1230-1240 may be performed to identify the respective contact 410 each of the electrodes 312 is connected to.

At step 1250, each of the electrodes 312 is associated with a different contact 410 based on the indication of the order in which the electrodes are arranged on the shaft 310 and the relative magnitudes of the output signals measured at each contact 410. As a result, each electrode 312 may be associated with a respective contact 410 which the electrode 312 is connected to via one of the wires 322. In some implementations, at step 1250, for each electrode 312, a different mapping may be generated that identifies the respective contact 410 to which the electrode 312 is connected.

In some implementations, each electrode 312 may be associated with a different contact 410. Additionally or alternatively, each electrode 312 may be associated with a contact 410 at which a voltage is measured that is commensurate with the position of that electrode 312 on the shaft 310. As a result, each electrode 312 that is the n-th closest to the distal end D of the shaft 310 may be associated with the contact 410 at which the n-th lowest voltage is measured, wherein n is a positive integer. Thus, the electrode 312 that is the closest to the distal end D may be associated with the electrode at which the lowest voltage is measured at step 1240, while the electrode 312 that is the furthest away from the distal end D may be associated with the contact 410 at which the highest voltage is measured.

At step 1260, a pinout map is generated that includes the respective mappings of each (or at least some) of the electrodes 312. At step 1270, the pinout map is stored in a memory device that is integrated into the catheter 500.

Figure 13A:
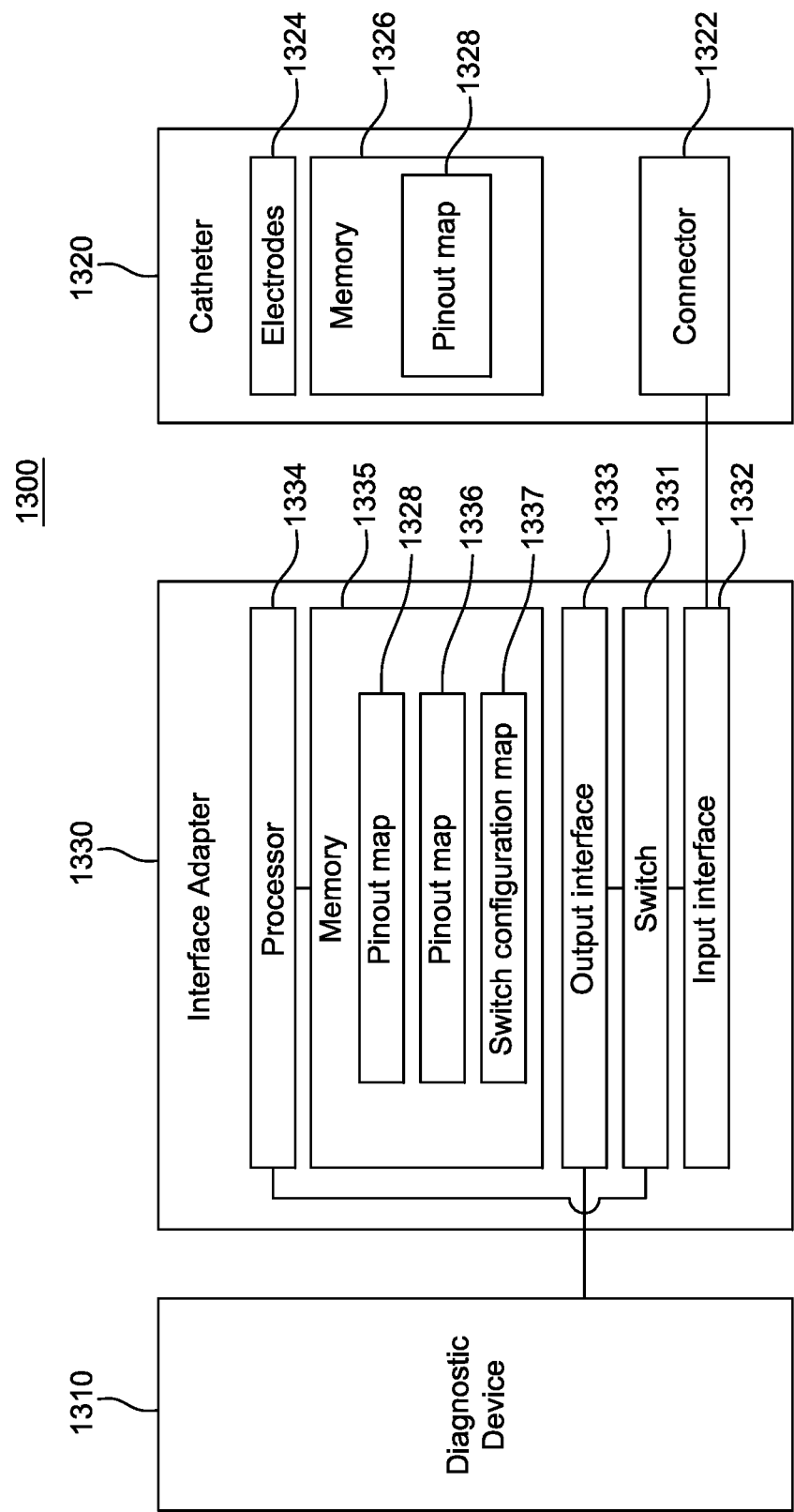
FIG. 13A is a diagram of an example of a system, according to aspects of the disclosure.

FIG. 13A is a diagram of an example of a system 1300, according to aspects of the disclosure. The system 1300 may be the same or similar to the system 200 shown in FIG. 2. More particularly, the system 1300 may include a diagnostic device 1310 that is connected to a catheter 1320 via an interface adapter 1330.

The diagnostic device 1310 may include any suitable type of device that is arranged to receive and/or interpret one or more signals that are generated using a diagnostic catheter. The diagnostic device 1310 may include an ECG monitor or a 3D Navigation System that calculates X, Y, or Z coordinates of catheter positions for example. The catheter 1320 may be any suitable type of diagnostic catheter, such as the Biosense Webster NAVISTAR® THERMOCOOL®, Biosense Webster LASSO®, Biosense DECARAY® catheter etc. The interface adapter 1330 may include a plug-and-play adapter that works effortlessly with the diagnostic device 1310 to allow access to different electrodes (and other features) of the catheter 1320 by changing the order in which signals received from the catheter are provided on different input channels of the diagnostic device 1310

In some implementations, the catheter 1320 may be the same or similar to the catheter 500, shown in FIG. 5. The catheter 1320 may include a connector 1322, a plurality of electrodes 1324, and a memory 1326. The connector 1322 may include a plurality of contacts. Each contact may be coupled at random to a different one of the plurality of electrodes 1324 via a different wire (not shown). The memory 1326 may include any suitable type of non-volatile memory, such as an EEPROM, a flash drive, or a solid-state drive, for example. The memory 1335 may be disposed inside the handle of the catheter 1320 (not shown) or in any other portion of the catheter 1320. Stored in the memory 1335 may be a pinout map 1328 which identifies the respective electrode each contact is connected to.

In some implementations, the pinout map 1328 may be the same or similar to the pinout map 700 shown in FIG. 7. In some implementations, the pinout map 1328 may be retrievable from the memory 1326 (by the diagnostic device 1310) via the connector 1322. In such instances, the same interface (e.g., the connector 1322) may be used to provide the pinout map 1328 to the diagnostic device, as well as feed to the diagnostic device 1310 signals from the electrodes 1324. Additionally or alternatively, in some implementations, the pinout map 1328 may be retrievable from the memory 1326 via an interface that is separate from the connector 1322. Additionally or alternatively, in some implementations, the pinout map 1328 may be generated in the manner discussed with respect to any of FIGS. 8-12.

The interface adapter 1330 may include a switch 1331, an input interface 1332, an output interface 1333, a processor 1334, and a memory 1335. The processor 1334 may be operatively coupled to any of the switch 1331, the input interface 1332, the output interface 1333, and the memory 1335.

The switch 1331 may be an electronic component and/or circuit that is capable of opening and closing each of a plurality of electrical paths. In the present example, the switch 1331 includes a plurality of input channels and a plurality of output channels. Each of the input channels can be selectively connected to any of the output channels, by the switch 1331, based one or more control signals that are received by the switch 1331 from the processor 1334.

The input interface 1332 may be any suitable type of connector or connector receptacle. In the present example, the input interface 1332 may be a connector receptacle that is arranged to mate with the connector 1322. The input interface 1332 may include a plurality of contacts. Each of these contacts may connect to a different one of the contacts in the connector 1322 when the connector 1322 is inserted into the input interface 1332. Moreover, each of the contacts in the input interface 1332 may be connected to a different input channel of the switch 1331.

The output interface 1333 may be any suitable type of connector or connector receptacle. In the present example, the output interface 1333 includes a connector that is arranged to mate with a connector receptacle on the diagnostic device 1310. The output interface 1333 may include a plurality of contacts. Each of these contacts may connect to a different contact of the input interface of the diagnostic device 1310 (not shown) when the interface adapter 1330 is connected to the diagnostic device 1310. Moreover, each of the contacts in the output interface 1333 may be connected to a different output channel of the switch 1331.

The processor 1334 may include one or more of a general-purpose processor (e.g., an ARM-based processor), an application specific integrated circuit (ASIC), a Field-Programmable Gate Array (FPGA), a complex programmable logic device (CPLD) and/or any other circuitry that is capable of causing the switch to close a plurality of electric paths between different ones of its input channels and respective output channels.

The memory 1335 may include any suitable type of volatile and/or non-volatile storage device. According to aspects of the disclosure, the memory 1335 may include one or more of an EEPROM memory, a random access memory (RAM), a flash memory, and a read-only memory, for example. During the operation of the system 1300, the memory 1335 may store one or more of the pinout map 1328, a pinout map 1336, and a switch configuration map 1337. In some implementations, the pinout map 1328 may be placed in the memory 1335 after it is retrieved from the catheter 1320 following the connection of the catheter 1320 to the interface adapter 1330, for example.

FIGS. 13B-C are diagrams illustrating examples of the pinout map 1328, the pinout map 1336, and the switch configuration map 1337, according to aspects of the disclosure. In the present example, each of the maps 1328, 1336, and 1337 is a table. However, alternative implementations are possible in which each of the maps 1328, 1336, and 1337 can be implemented as another type of data structure.

The pinout map 1328 specifies the order in which the electrodes 1324 are connected to the contacts of the connector 1322. The pinout map 1328 includes a plurality of mappings 1328a. Each mapping 1328a includes an identifier of one of the electrodes 1324 and an identifier of a respective contact in the connector 1322 which the electrode is connected to. In some implementations, the identifier of any of the electrodes 1324 may include one or more numbers and/or symbols that indicate, either implicitly or explicitly, the identity of that electrode. For instance, the identifier of any of the electrodes may include an indication of a type of signal that is produced by the electrode, an indication of the type of the electrode, an indication of the position of the electrode on the shaft of the catheter 1320, etc. In some implementations, the identifier of any of the contacts of the connector 1322 may include one or more numbers and/or symbols that indicate, either implicitly or explicitly, the identity of a particular contact. For instance, the identifier of any of the contacts may include an indication of an output channel that is associated with the contact, a pin number, etc. To illustrate how the pinout map 1328 relates to the pinout map 1336 and the switch configuration map 1337, in FIG. 13B, under the identifier of each contact in the connector 1322, in parenthesis, a contact of the input interface 1332 is identified that is connected to the contact of the connector 1322 when the catheter 1320 is coupled to the interface device 1330.

The pinout map 1336 specifies an interface standard supported by the diagnostic device 1310. More particularly, the pinout map specifies the order in which the signals from the electrodes 1324 need to be applied at different contacts of an input interface (not shown) of the diagnostic device 1310 that is coupled to the output interface 1333 of the interface adapter 1330 in order of the diagnostic device 1310 to be able to use the signals for diagnostic purposes. In the present example, the pinout map 1336 includes a plurality of mappings 1336a. Each mapping 1336a includes an identifier of one of the electrodes 1324 and an identifier of a respective contact in the output interface 1333 which the electrode needs to be connected to in order for the interface adapter 1330 to comply with the interface standard supported by the diagnostic device 1310. To illustrate how the pinout map 1336 relates to the pinout map 1328 and the switch configuration map 1337, in FIG. 13B, under the identifier of each contact in the in the input interface of the diagnostic device 1310, in parenthesis, a contact of the output interface 1333 is identified that is connected to the contact of the diagnostic device 1310 when the interface device 1330 is coupled to the diagnostic device 1310.

In some implementations, the identifier of any of the electrodes 1324 in each mapping 1336a of the pinout map 1336 may include one or more numbers and/or symbols that indicate, either implicitly or explicitly, the identity of that electrode. For instance, the identifier of any of the electrodes may include an a type of signal that is produced by the electrode, an indication of the type of the electrode, an indication of the position of the electrode on the shaft of the catheter 1320, etc. In some implementations, the identifier of each of the contacts of the diagnostic device 1310 may include one or more numbers and/or symbols that indicate, either implicitly or explicitly, the identity of that contact. For instance, the identifier of any of the contacts may include an indication of an input channel of the diagnostic device 1310 that is associated with the contact, an output channel (e.g., of a catheter or interface adapter) that is associated with the contact, a contact in the output interface 1333 of the interface adapter 1330, a pin number corresponding to a first input pin of the diagnostic device 1310, a pin number corresponding to a second output pin of the output interface 1333 which comes in contact with the first input pin when the interface adapter 1330 is connected to the diagnostic device 1310, etc.

The switch configuration map 1337 specifies a state which the switch 1331 needs to enter in order for the signals from the electrodes 1324 to be output on the output interface 1333 in the order specified by the pinout map 1336. More particularly, the switch configuration map 1337 specifies a state of the switch 1331 in which the switch is operable to route the signal from each of the electrodes 1324 to a different contact in the output interface 1333 that is specified (implicitly or explicitly) for the electrode by the pinout map 1336.

The switch configuration map 1337 includes a plurality of mappings 1337a. Each mapping 1337a includes an identifier of an input channel of the switch 1331 and an identifier of an output channel of the switch 1331 which the input channel needs to be connected to by the switch 1331. As discussed further below, the switch configuration map 1337 may be generated by the processor 1334 based on at least one of the pinout map 1328 and the pinout map 1336. The processor 1334 may configure the switch 1331 in accordance with the switch configuration map 1337 in order to route the signal from each electrode 1324 to the contact in the output interface 1333 that is specified (implicitly or explicitly) for that electrode by the pinout map 1336. More particularly, the processor 1334 may generate and provide one or more control signals to the switch 1331 based on the switch configuration map 1337, which when received by the switch 1331 cause the switch to connect its each of its input channels with a respective output channel identified by the switch configuration map 1337.

Figure 14:
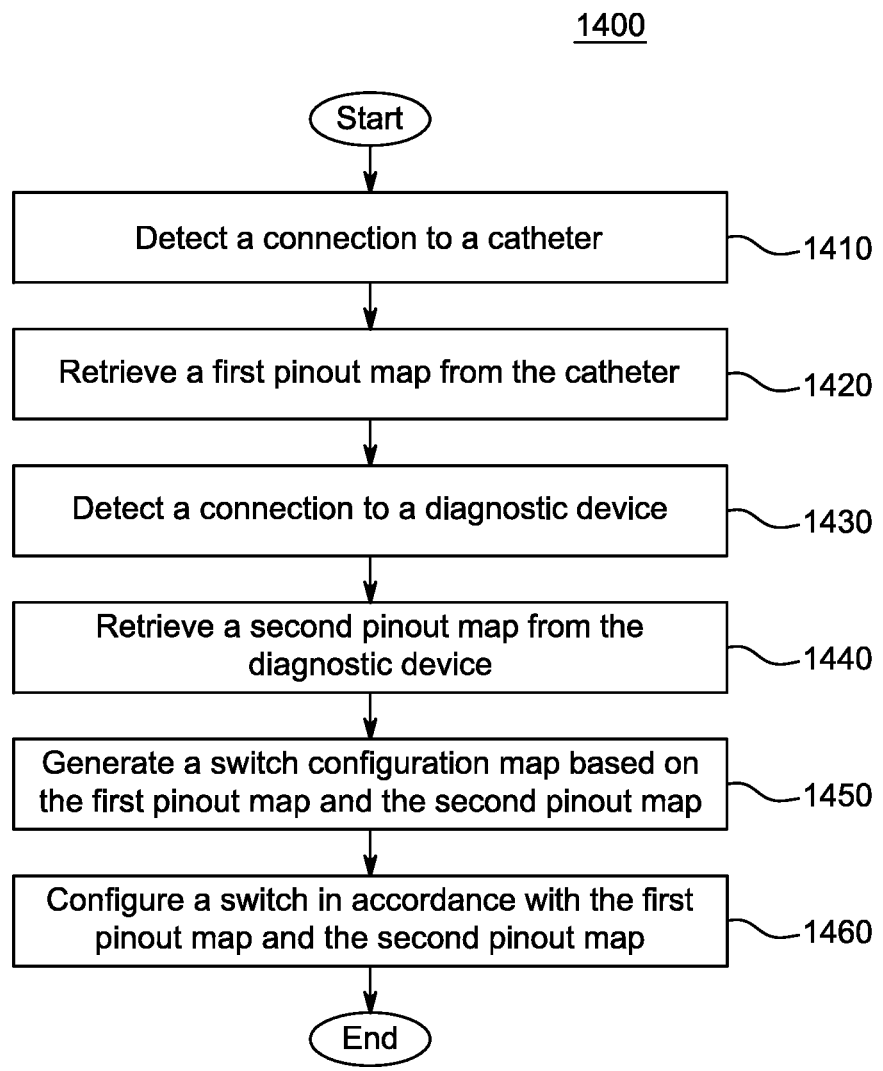
FIG. 14 is a flowchart of an example of a process performed by one or more devices in the system of FIG. 13A, according to aspects of the disclosure.

FIG. 14 is a flowchart of an example of a process 1400 which is performed by the interface adapter 1330, according to aspects of the disclosure.

At step 1410, the processor 1334 detects that the interface adapter 1330 is connected to the catheter 1320 via the input interface 1332. At step 1420, in response to detecting the connection with the catheter 1320, the processor 1334 retrieves the pinout map 1336 from the memory 1326. The pinout map 1336 may be retrieved using the connector 1322 of the catheter 1320. However, alternative implementations are possible in which the pinout map 1336 is retrieved via a wireless interface or another wired interface.

At step 1430, the processor 1334 detects that the interface adapter 1330 is connected to the diagnostic device via the output interface 1333. At step 1440, the interface adapter 1330 retrieves the pinout map 1336 from the diagnostic device 1310. Although in the present example the pinout map 1336 is retrieved from the diagnostic device 1310, alternative implementations are possible in which the pinout map 1336 is pre-stored in the memory 1335.

At step 1450, the processor 1334 generates the switch configuration map 1337 based on at least one of the pinout map 1328 and the pinout map 1336. In some implementations, the switch configuration map 1337 may be generated by cross-referencing the pinout map 1328 with the pinout map 1336. In some implementations, the cross-referencing may be performed by using an additional data structure that indicates the order in which the input contacts of diagnostic device 1310 are connected to the output channels of the switch 1331 when the interface adapter 1330 is coupled to the diagnostic device 1310. More particularly, in some implementations, generating the pinout map may include performing the following tasks for each electrode 1324 in the catheter 1320: (a) identifying a first contact in the connector 1322 which the electrode is connected to, (b) identifying an input channel of the switch 1331 which the first contact is connected to, (c) identifying a second contact in the output interface 1333 which the electrode needs to be connected to, (d) identifying an output channel of the switch 1331 that is connected to the second contact in the output interface 1333, (e) creating a mapping 1337*a* associating the identified input channel of the switch 1331 with the identified output channel of the switch 1331, and (f) including the mapping in the switch configuration map 1337.

At step 1460, the processor 1334 configures the switch 1331 in accordance with the switch configuration map 1337. More particularly, the interface adapter 1330 causes the switch 1331 to connect each output channel in the switch 1331 to a different input channel of the switch 1331 that is identified by the switch configuration map 1337. In some implementations, configuring the switch may include performing the following tasks once for each one of the mappings 1337*a* in the switch configuration map 1337: (a) identifying an input channel that is indicated by the mapping, (b) identifying an output channel that is indicated by the mapping, and (c) transmitting a control signal to the switch 1331 that causes the switch to connect the identified output channel to the identified input channel.

The process 1400 is provided as an example only. Although in the present example the switch configuration map is used to reconfigure the switch, alternative implementations are possible in which no switch configuration map is generated or used. In such instances, the input channels of the switch 1331 may be connected to one-by-one to corresponding output channels based on at least one of the pinout map 1328 and the pinout map 1336.

Figure 15A:
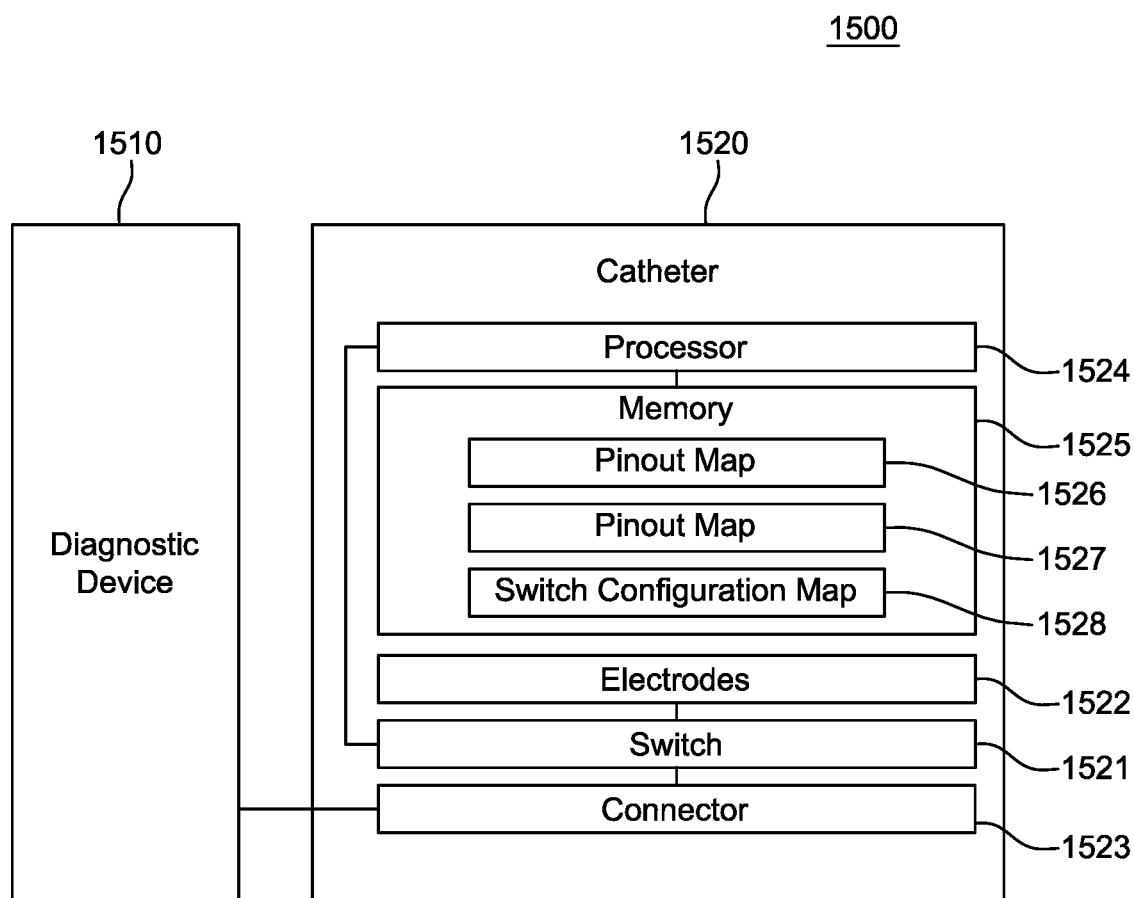
FIG. 15A is a diagram of an example of a system, according to aspects of the disclosure.

FIG. 15A is a diagram of an example of a system 1500 according to aspects of the disclosure. The system 1500 may include a diagnostic device 1510 and a catheter 1520. The diagnostic device 1510 may include any suitable type of device that is arranged to receive and/or interpret one or more signals that are generated using a diagnostic catheter. The diagnostic device 1510 may include an ECG monitor, or a 3D Navigation System that calculates X, Y, or Z coordinates of catheter positions for example. The catheter 1520 may be any suitable type of diagnostic catheter, such as the Biosense Webster NAVISTAR® THERMOCOOL®, Biosense Webster LASSO®, Biosense DECARAY® catheter etc. In some implementations, the catheter 1320 may be the same or similar to the catheter 500, shown in FIG. 5.

The catheter 1520 may include a switch 1521, a plurality of electrodes 1522, a connector 1523, a processor 1524, and a memory 1525. The processor 1524 may be operatively coupled to any of the switch 1521, the connector 1523, and the memory 1525.

The switch 1521 may be an electronic component and/or circuit that is capable of capable of opening and closing each of a plurality of electrical paths. In the present example, the switch 1521 includes a plurality of input channels and a plurality of output channels. Each of the input channels may be connected to a different electrode 1522 via one or more wires (not shown). Furthermore, each of the input channels can be selectively connected to any of the output channels, by the switch 1521, based one or more control signals that are received from the processor 1524.

The connector 1523 may include any suitable type of connector. In some implementations, the connector 1523 may be the same or similar to the connector 400, which is discussed with respect to FIG. 4. Additionally or alternatively, the connector 1523 may include a plurality of contacts. The contacts may be the same or similar to the contacts 410 of the connector 400. Each of the contacts may be connected to a different output channel of the switch 1521.

Although in the present example a connector is used as the output interface of the catheter 1520, alternative implementations are possible in which another type of output interface is used, such as a receptacle or a wireless output interface.

The processor 1524 may include one or more of a general-purpose processor (e.g., an ARM-based processor), an application specific integrated circuit (ASIC), a Field-Programmable Gate Array (FPGA), a complex programmable logic device (CPLD) and/or any other circuitry that is capable of causing the switch to close a plurality of electric paths between different ones of its input channels and respective output channels.

The memory 1525 may include any suitable type of volatile and/or non-volatile storage device. According to aspects of the disclosure, the memory 1525 may include one or more of an EEPROM memory, a random access memory (RAM), a flash memory, and a read-only memory, for example. In some implementations, the memory 1525 may store one or more of a pinout map 1526, a pinout map 1527, and a switch configuration map 1528.

Figure 15C:
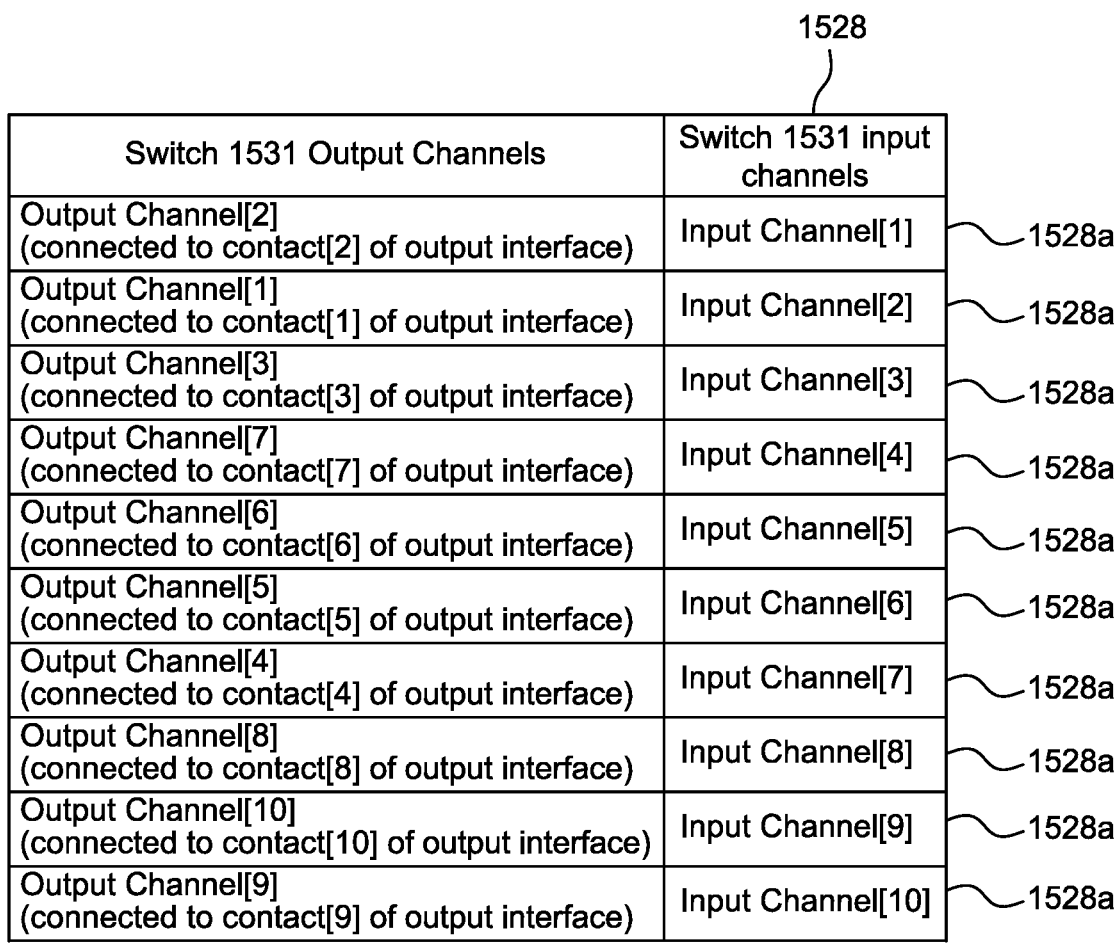
FIG. 15C is a diagram of an example of a data structure used by the system of FIG. 15A, according to aspects of the disclosure.

FIGS. 15B-C depict examples of the pinout map 1526, the pinout map 1527, and the switch configuration map 1528. In the present example, each of the maps 1526, 1527, and 1528 is a table. However, alternative implementations are possible in which each of the maps 1526, 1527, and 1528 can be implemented as another type of data structure.

The pinout map 1526 may specify the order in which the electrodes 1324 are connected to the input channels of the switch 1521. The pinout map 1526 may include a plurality of mappings 1526*a*. Each mapping 1526*a* may identify one of the electrodes 1522 and indicate an input channel of the switch 1521 (or another element of the catheter 1520) which the electrode is connected to. In some implementations, the identifier of any of the electrodes 1522 may include one or more numbers and/or symbols that indicate, either implicitly or explicitly, the identity of that electrode. For instance, the identifier of any of the electrodes may include an indication of a type of signal that is produced by the electrode, an indication of the type of the electrode, an indication of the position of the electrode on the shaft of the catheter 1520, etc. In some implementations, the pinout map 1526 may be generated and stored in the memory 1525 in the manner discussed with respect to FIGS. 1-12.

The pinout map 1527 specifies an interface standard supported by the diagnostic device 1510. More particularly, the pinout map 1527 may specify the order in which the signals from the electrodes 1522 need to be applied at different contacts of an input interface (not shown) of the diagnostic device 1510 that is coupled to the connector 1523 in order of the diagnostic device 1510 to be able to use the signals for diagnostic purposes. In the present example, the pinout map 1527 includes a plurality of mappings 1527*a*. Each mapping 1527*a* may identify one of the electrodes 1522 and indicate one of the contacts in the input interface of the diagnostic device 1510 (not shown) on which signals from the electrode need to be output. To illustrate how the pinout map 1527 relates to the pinout map 1526 and the switch configuration map 1528, in FIG. 15C, under the identifier of each contact in the in the input interface of the diagnostic device 1510, in parenthesis, a contact of the connector 1523 of the catheter 1520 is identified that is connected to the contact of the diagnostic device 1510 when the catheter 1520 is coupled to the diagnostic device 1510.

In some implementations, the identifier of each of the electrodes 1522 in any mapping 1527*a* of the pinout map 1527 may include one or more numbers and/or symbols that indicate, either implicitly or explicitly, the identity of the electrode. For instance, the identifier of any of the electrodes may include an indication of a type of signal that is produced by the electrode, an indication of the type of the electrode, an indication of the position of the electrode on the shaft of the catheter 1520, etc. In some implementations, the identifier of any of the contacts input interface of the diagnostic device 1510 may include one or more numbers and/or symbols that indicate, either implicitly or explicitly, the identity of the contact. For instance, the identifier of any of the contacts may include an indication of an output channel of the catheter 1520 that is associated with the contact, an indication of an input channel of the diagnostic device 1310, a pin number corresponding to a first input pin of the diagnostic device 1510, a pin number corresponding to a second output pin of the connector 1523 which comes in contact with the first input pin when the connector 1523 is connected to the diagnostic device 1510, etc.

The switch configuration map 1528 specifies a state which the switch 1521 needs to enter in order for the signals from the electrodes to be output by the connector 1523 in the order specified by the pinout map 1527. More particularly, the switch configuration map 1528 specifies a state of the switch 1521 in which the switch is operable to route the signal from each of the electrodes 1522 to a different contact in the connector 1523 that is specified by the pinout map 1527. In the present example, the switch configuration map 1528 includes a plurality of mappings 1528*a*. Each mapping 1528*a* identifies an input channel of the switch 1531 and a respective output channel of the switch 1531 which the input channel needs to be connected to.

Figure 16:
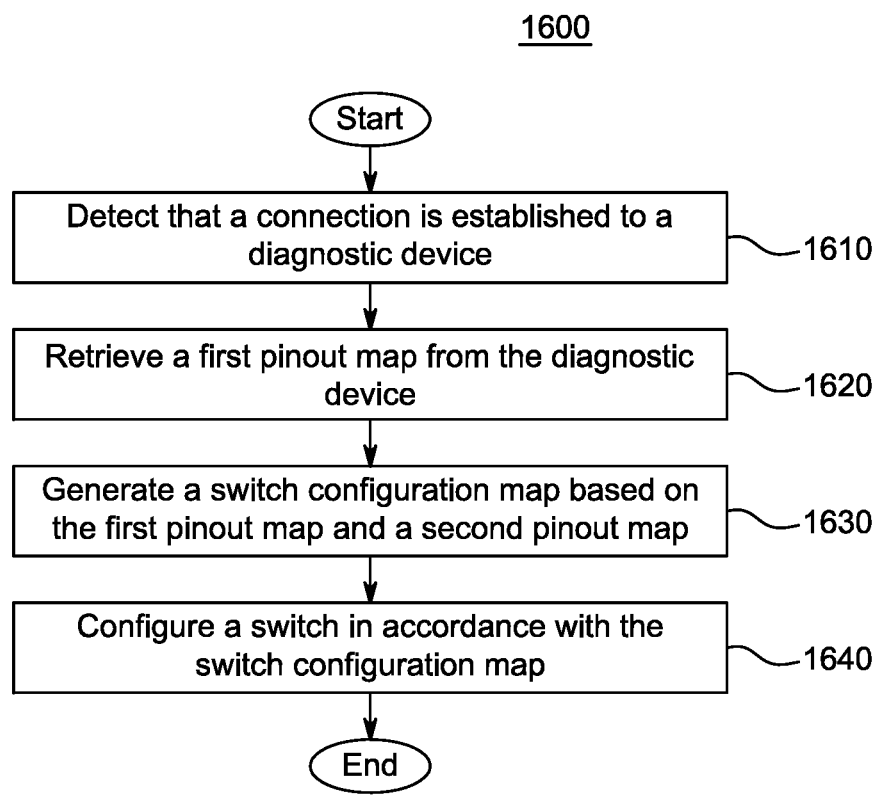
FIG. 16 is a flowchart of an example of a process performed by one or more devices in the system of FIG. 15A, according to aspects of the disclosure.

FIG. 16 is flowchart of an example of a process 1600 performed by the catheter 1520, according to aspects of the disclosure.

At step 1610, the processor 1524 detects that a connection is established between the catheter 1520 and the diagnostic device 1510. In some implementations, the connection may be established as a result of the connector 1523 being plugged into the diagnostic device 1510.

At step 1620, the processor 1524 retrieves the pinout map 1527 from the diagnostic device 1510. Although in the present example the pinout map 1527 is retrieved from the diagnostic device 1510, alternative implementations are possible in which the pinout map 1527 is pre-stored in the memory 1525.

At step 1630, the processor 1524 generates the switch configuration map 1528 based on at least one of the pinout map 1526 and the pinout map 1527. In some implementations, the switch configuration map 1528 may be generated by cross-referencing the pinout map 1526 with the pinout map 1527. In some implementations, the cross-referencing may be performed by using an additional data structure that indicates the order in which the input contacts of diagnostic device 1510 are connected to the output channels of the switch 1521 when the catheter 1520 is coupled to the diagnostic device 1510. More particularly, in some implementations, generating the pinout map may include performing the following tasks once for each electrode 1522 in the catheter 1520: (a) identifying an input channel of the switch 1521 which the electrode is connected to, (b) identifying a contact in the connector 1523 which the electrode needs to be connected to, (d) identifying an output channel of the switch 1521 that is connected to the second contact, (e) creating a mapping 1528*a* associating the identified input channel of the switch 1521 with the identified output channel of the switch 1521, and (f) including the mapping in the switch configuration map 1528.

At step 1640, the processor 1524 configures the switch 1521 in accordance with the switch configuration map 1528. More particularly, the processor 1524 may cause the switch 1521 to connect each of its output channels to a different input channel of the switch 1521 that is identified by the switch configuration map 1528. In some implementations, configuring the switch may include performing the following tasks once for each mapping 1528*a* in the switch configuration map 1528: (a) identifying an input channel of the switch 1521 that is indicated by the mapping, (b) identifying an output channel that is indicated by the mapping, and (c) transmitting a control signal to the switch 1521 that causes the switch 1521 to connect the identified output channel to the identified input channel.

The process 1600 is provided as an example only. Although in the present example the switch configuration map is used to reconfigure the switch, alternative implementations are possible in which no switch configuration map is generated. In such instances, the input channels of the switch 1521 may be connected to one-by-one to corresponding output channels based at least on at least one of the pinout map 1526 and the pinout map 1527.

Figure 17:
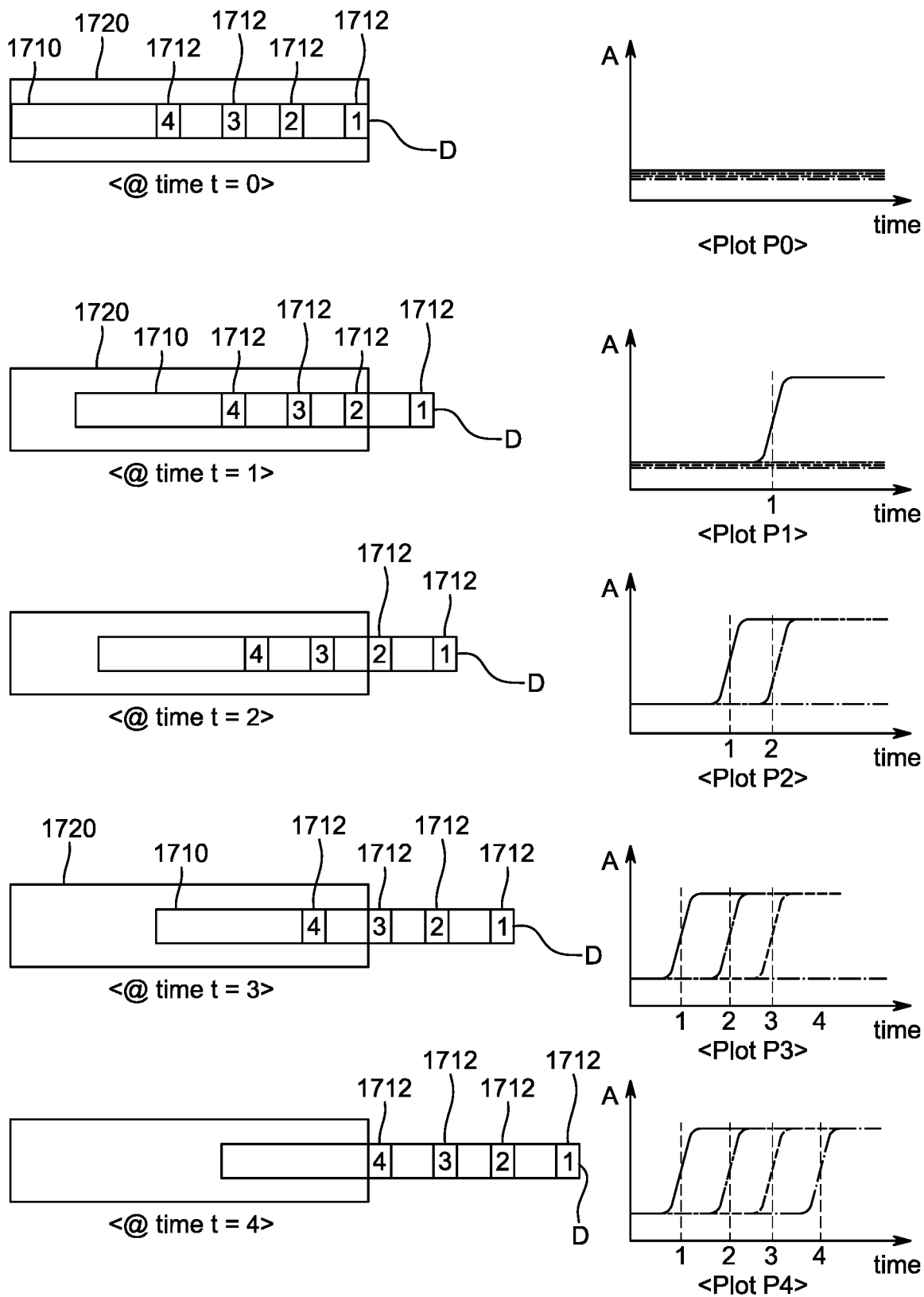
FIG. 17 is a diagram illustrating an example of a process for configuring a catheter, according to aspects of the disclosure.

FIG. 17 is a diagram illustrating another technique for associating electrodes (or signals) with different input channels at a diagnostic device. This technique may be performed by any diagnostic device, while the diagnostic device is being used in conjunction with a catheter to examine a patient.

In some aspects, when a catheter is inserted into a patient's body it is contained in a sheath. The sheath is a plastic tube of larger diameter than the catheter which is used to limit pain and increase accuracy. The catheter stays in the sheath until the location is reached where the catheter needs to be deployed (e.g., the patient's heart). At this point, the end of the catheter which contains electrodes is slid out of the sheath to enter the location. Because the electrodes are arranged in a line on the end of the catheter, they leave the sheath one after another. When each electrode leaves the sheath, the value of the signal provided by that electrode changes. Thus, the order in which the signals provided by the electrodes change matches the order in which the electrodes are arranged on the catheter. Accordingly, by monitoring the order in which the signals change, it is possible to identify the electrode that generated each of the signals.

Shown in FIG. 17 is a catheter 1710 that is at first fully contained in a sheath 1720. For the purposes of this example, the sheath 1720 has been inserted up to the location (e.g., a heart chamber) where the catheter needs to be deployed. The catheter 1710 includes a plurality of electrodes 1712 disposed on a shaft. When the shaft is slid out of the sheath 1720, the electrodes 1712 exit the sheath one after another.

At time t=0, all electrodes 1712 are situated in the sheath 1720 and the diagnostic device receives a respective signal from each of the electrodes 1712. Each signal is received on a different input channel of the diagnostic device. The signals received from the electrodes are shown in plot P0.

At time t=1, a first electrode 1712 exits the sheath 1720 and comes in contact with the environment surrounding the sheath 1720 (e.g., the patient's tissue, etc.). As a result, the signal provided by this electrode changes (e.g., its value increases). The change is shown in plot P1. The diagnostic device detects that this is the first signal change that takes place during the exit of the catheter 1710 from the sheath 1720 and associates the input channel on which the signal is received with the first electrode on the catheter 1710 (e.g., the electrode that is the closest to the distal end D of the catheter).

At time t=2, the second electrode 1712 exits the sheath 1720 and comes in contact with the environment surrounding the sheath 1720 (e.g., the patient's tissue, etc.). As a result, the signal provided by this electrode changes (e.g., its value increases). The change is shown in plot P2. The diagnostic device detects that this is the second signal change that takes place during the exit of the catheter 1710 from the sheath 1720 and associates the input channel on which the changed signal is received with the second electrode 1712 on the catheter 1710 (e.g., the electrode that is second closest to the distal end D of the catheter).

At time t=3, the third electrode 1712 exit the sheath 1720 and comes in contact with the environment surrounding the sheath 1720 (e.g., the patient's tissue, etc.). The change is shown in plot P3. The diagnostic device detects that this is the third signal change that takes place during the exit of the catheter 1710 from the sheath 1720 and associates the input channel on which the changed signal is received with the third electrode 1712 on the catheter 1710 (e.g., the electrode that is third closest to the distal end D of the catheter).

At time t=4, the fourth electrode 1712 exits the sheath 1720 and comes in contact with the environment surrounding the sheath 1720 (e.g., the patient's tissue, etc.). As a result, the signal provided by the fourth electrode changes (e.g., its value increases). The change is shown in plot P4. The diagnostic device detects that this is the second signal change that takes place during the exit of the catheter 1710 from the sheath 1720 and associates the input channel on which the changed signal is received with the fourth electrode 1712 on the catheter 1710 (e.g., the electrode that is fourth closest to the distal end D of the catheter).

Figure 18:
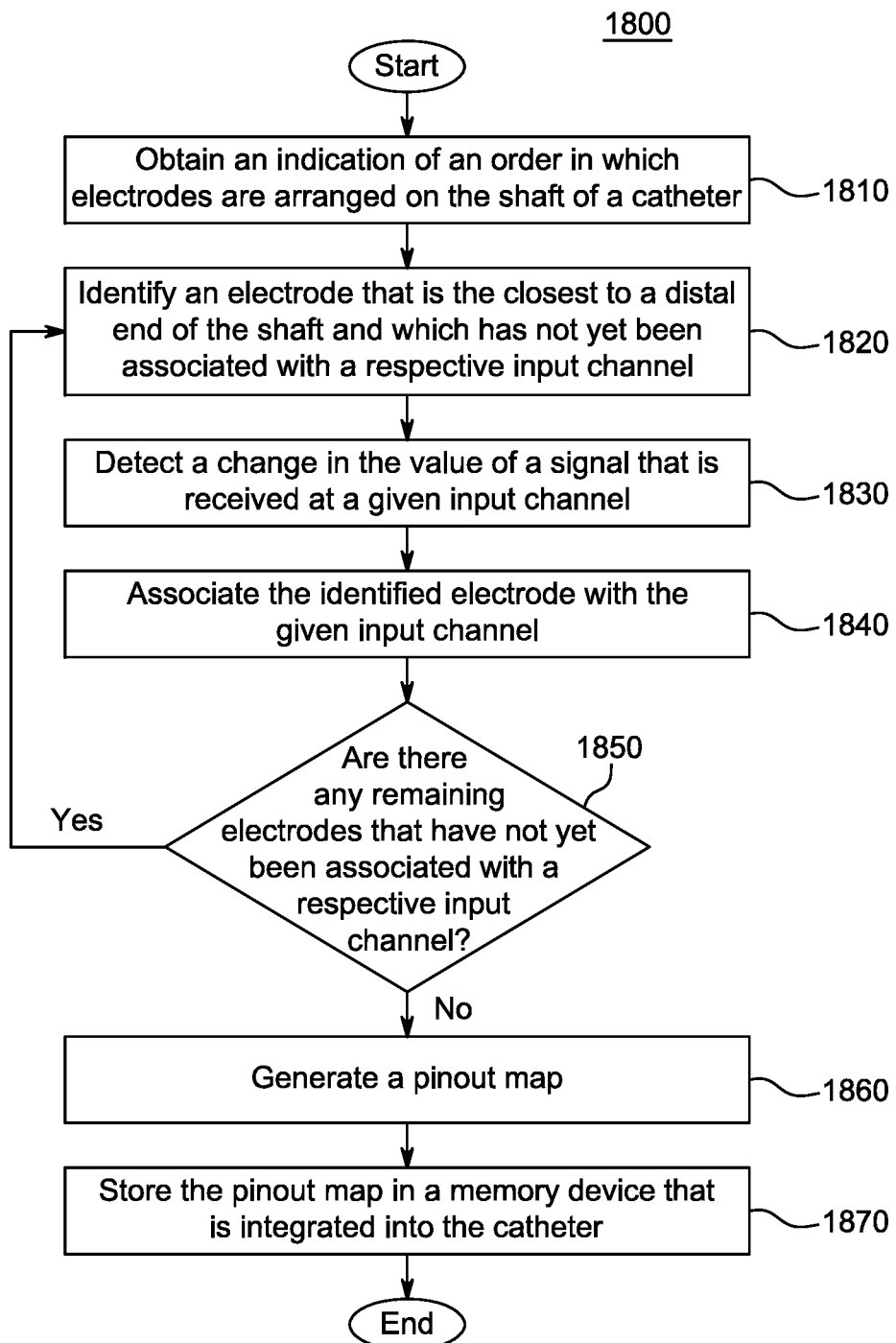
FIG. 18 is a flowchart of an example of a process for configuring a catheter, according to aspects of the disclosure.

FIG. 18 is a flowchart of an example of a process 1800, according to aspects of the disclosure. The process 1800 implements the technique discussed above with respect to FIG. 17 and it can be performed by a diagnostic device connected to the catheter 1710.

At step 1810, an indication is obtained of an order in which the electrodes 1712 are arranged on the shaft of the catheter 1710. In some implementations, the indication may include a set of identifiers. As illustrated in FIG. 17, each identifier may include a different number. All electrodes having identifiers that are smaller than the identifier of a given electrode may be located closer than the given electrode to the distal end of the shaft of the catheter 1710. Similarly, all electrodes having identifiers that are larger than the identifier of the given electrode may be located further away than the given electrode from the distal end D of the catheter 1710. Additionally or alternatively, in some implementations, the indication may include an ordered list of electrode identifiers. Each identifier in the list may correspond to a different electrode. The position of each identifier in the list may correspond to the position of the identifier's electrode 1712 on the shaft of the catheter 1710. For instance, the closer a given electrode 1712 is to the distal end D of the shaft of the catheter 1710, the closer the electrode's identifier may be to the beginning of the list.

At step 1820, an electrode 1712 is identified that is the closest one to the distal end D of the catheter 1710 that has not yet been associated with a respective input channel of the diagnostic device. At step 1830, a change in the value of a signal received at one of the input channels of the diagnostic device is detected. The change may include either an increase or a decrease in the value of the signal. Additionally or alternatively, in some implementations, the change may be detected in response to the value of the signal crossing a threshold and/or remaining stable for a predetermined time period.

At step 1840, the input channel on which the signal change is detected is associated with an electrode 1712 that is identified at step 1820. In some implementations, associating the electrode 1712 with the input channel may include generating a mapping that indicates that the electrode 1712 is connected to the input channel. The mapping may include any suitable type of number, string, and/or data structure. In some implementations, the mapping may include a first identifier of the electrode 1712 that is identified at step 1820 and a second identifier of the input channel, of the device executing the process 1800, at which the signal change is detected.

In some implementations, the identifier of any of the electrodes 1712 may include one or more numbers and/or symbols that indicate, either implicitly or explicitly, the identity of that electrode. For instance, the identifier of any of the electrodes may include an indication of a type of signal that is produced by the electrode, an indication of the type of the electrode, an indication of the position of the electrode on the shaft of the catheter 1710, etc. In some implementations, the identifier of any of the input channels of the diagnostic device may include one or more numbers and/or symbols that indicate, either implicitly or explicitly, the identity of a particular contact. For instance, the identifier of any of the input channels may include an indication of an input channel number, an indication of output channel of the catheter 1710 that is connected to input channel when the catheter 1710 is plugged into the diagnostic device, a pin number corresponding to a first input pin of the diagnostic device, a pin number corresponding to a second output pin of the catheter 1710 which comes in contact with the first input pin when the catheter 1710 is connected to the diagnostic device, etc.

At step 1850, a determination is made if there are any remaining electrodes 1712 that have not yet been associated with respective input channels. If there are such remaining electrodes, steps 1820-1840 are repeated again for another electrode. If there are no such remaining electrodes, at step 1860, a pinout table is generated that encapsulates each mapping that is generated at steps 1820-1840. At step 1870, the pinout table is stored in a memory device that is integrated into the catheter 1710.

According to aspects of the disclosure, the technique discussed with respect to FIGS. 17-18 may be advantageous because it does not require the catheter 1710 to include an integrated memory device. Rather, if desired, the technique permits a pinout map to be generated dynamically by a diagnostic device every time the catheter is 1710 is used, together with the diagnostic device, to diagnose a patient. Accordingly, the technique discussed with respect to the process of FIGS. 17-18 permits catheters whose electrodes are connected at random (e.g., random pinout catheters) to be used without the integration of additional hardware in those catheters, such as an integrated memory device, an integrated controller, and/or integrated switch, for example.

Additionally or alternatively, in some implementations, a configuration device, such as the configuration device 800, may be adapted to use the technique discussed with respect to FIGS. 17-18 to generate a pinout map for a catheter and store the pinout map in a memory device that is integrated into the catheter. More particularly, the configuration device may include an enclosure, a catheter receptacle (e.g., a hole), a receptacle for the catheter's connector, and a radio transmitter that is disposed in the disclosure. After the electrodes of the catheter have been connected at random, the catheter may be placed in a sheath and inserted into the shaft receptacle together with the sheath. After the sheath and the catheter have been inserted into the enclosure of the configuration device, through the receptacle, the end of the catheter which contains the electrodes may be slid out of the sheath. Because the electrodes are arranged in a line on the end of the catheter, they may leave the sheath one after another. When each electrode leaves the sheath, that electrode may act as an antenna and pick up a radio signal that is being transmitted by the radio transmitter. As a result, the value of the signal provided by that electrode at the connector receptacle may change. Afterwards, by monitoring the order in which the signals provided by the electrodes change, the configuration device may generate a pinout map in the manner discussed with the process of FIG. 18, and store the pinout map in a memory device that is integrated into the catheter. Additionally or alternatively, in some implementations, the catheter may be inserted into the configuration device without the sheath.

Figure 19:
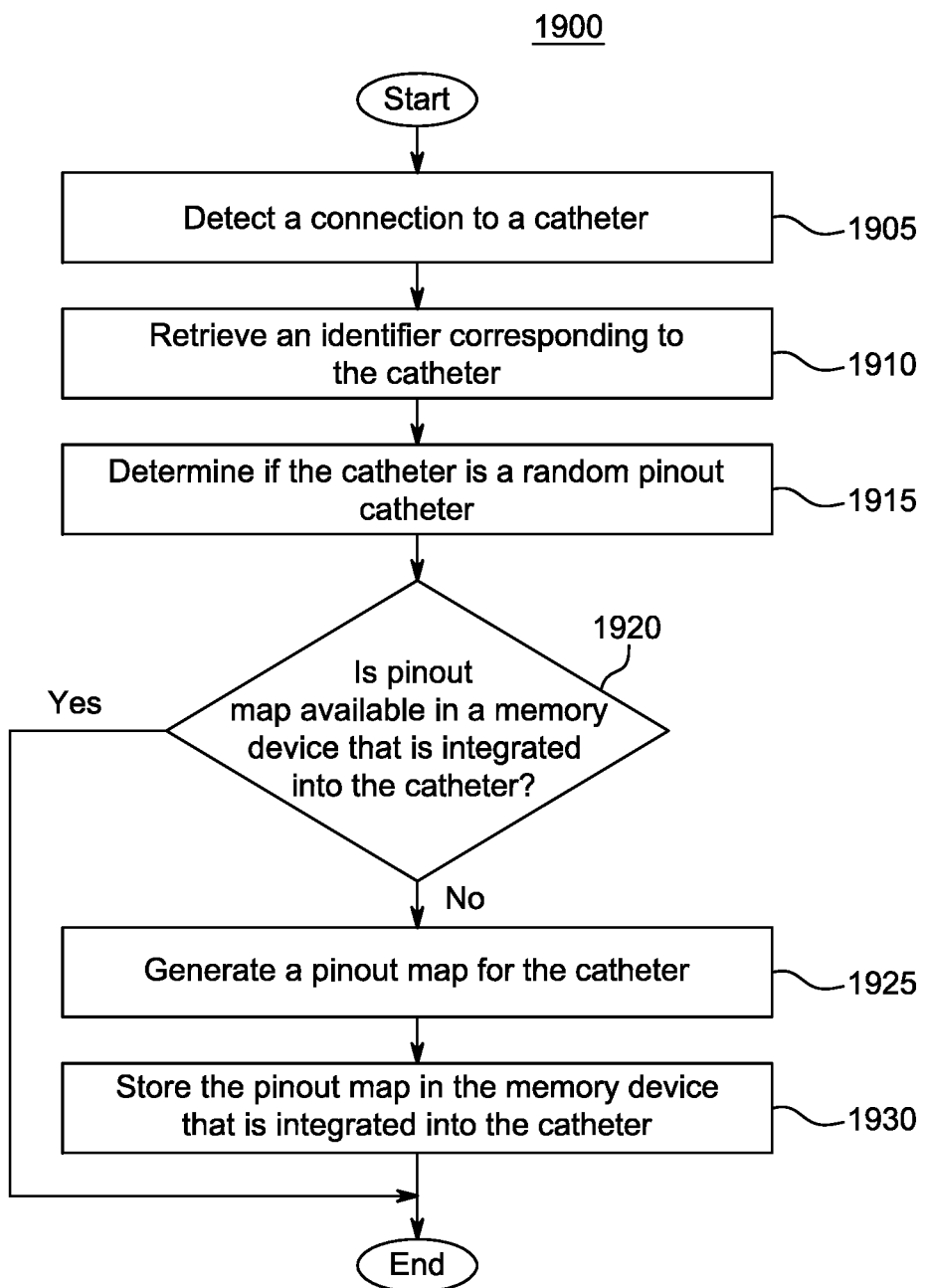
FIG. 19 is a flowchart of another example of a process for configuring a catheter, according to aspects of the disclosure.

FIG. 19 is a flowchart of another example of a process 1900, according to aspects of the disclosure. The process 1900 may be performed by a diagnostic device connected to a catheter and/or any other suitable type of device.

At step 1905, the diagnostic device detects that a catheter is connected to it. At step 1910, the diagnostic device retrieves an identifier of the catheter. At step 1915, a determination is made whether the catheter is a random pinout catheter based on the identifier. According to aspects of the disclosure, a random pinout catheter is a catheter whose electrodes have been connected at random to different contacts of a connector and/or a catheter that does not comply with any interface standard supported by the device executing the process 1900 (and/or another device on which the catheter is intended to be used). If the catheter is not a random pinout catheter, the process 1900 is terminated, after which the diagnostic device begins using the catheter in a well-known fashion. If the catheter is a random pinout catheter, the process proceeds to step 1920.

At step 1920, an attempt is made by the diagnostic device to retrieve, from a memory device that is integrated into the catheter, a pinout map that associates each of a plurality of electrodes in the catheter with a respective output channel of the catheter (e.g., a contact in the catheter's connector). If the attempt is successful, the process 1900 is terminated, after which the diagnostic device begin using the catheter in conjunction with the pinout table. If the attempt is unsuccessful, the process proceeds to step 1925.

At step 1925, the diagnostic device begins monitoring the signals received from the plurality of electrodes and generates a pinout map for the catheter. As discussed above, the pinout map may include a plurality of mappings. Each mapping may identify a different input channel on the diagnostic device and an electrode of the catheter that is connected to that channel. The pinout map may be generated in accordance with the process 1800 which is discussed above with respect to FIG. 18.

At step 1930, the pinout table is stored in a memory device that is integrated into the catheter. As a result, next time the catheter is plugged into the diagnostic device, the catheter can be used without having to perform step 1925 again. Furthermore, after the pinout table is stored in the catheter, the catheter may be used on less expensive diagnostic devices that potentially lack the capability to perform step 1925 and/or the process 1800 on their own.

FIGS. 1-19 are provided as an example only. Although in various examples throughout the disclosure, a random pinout catheter is connected to a diagnostic device via a connector, it will be understood that any suitable type of connection interface can be used by the random pinout catheter instead. Accordingly, the random pinout catheters discussed above can use any suitable type of connection interface (e.g., wired or wireless, male or female, etc.) to connect to interface devices and/or diagnostic devices. In instances in which a wireless connection interface is used, the pinout maps discussed above can identify wireless channels and/or virtual channels instead of connector contacts. Furthermore, the pinout maps may be implemented in any suitable manner. Although in the examples throughout the disclosure, multiple mappings are encapsulated in the same data structure, alternative implementations are possible in which each mapping is stored separately from the rest. For example, each mapping may be stored as a separate file in the same file system directory. Furthermore, the present disclosure is not limited to any particular technique for encoding the information represented by the mappings. Although in the above examples, each mapping includes two identifiers, alternative implementations are possible in which each mapping consists of a single number and/or string which in which the two identifiers are encoded. At least some of the elements discussed with respect to these figures can be arranged in different order, combined, and/or altogether omitted. It will be understood that the provision of the examples described herein, as well as clauses phrased as "such as," "e.g.", "including", "in some aspects," "in some implementations," and the like should not be interpreted as limiting the disclosed subject matter to the specific examples.

Having described the invention in detail, those skilled in the art will appreciate that, given the present disclosure, modifications may be made to the invention without departing from the spirit of the inventive concepts described herein. Therefore, it is not intended that the scope of the invention be limited to the specific embodiments illustrated and described.

What is claimed is:

1. A catheter, comprising:
   a connector including a plurality of first contacts and one or more second contacts laterally spaced therefrom;
   a shaft including a plurality of electrodes, each electrode being coupled to a different one of the plurality of first contacts; and
   a memory coupled to at least one of the one or more second contacts, wherein the memory is configured to:
      store a pinout map identifying an order in which the plurality of electrodes has been coupled to the plurality of first contacts, wherein the catheter is configured so that any electrode can be coupled to any first contact while maintaining usability; and
      provide the pinout map to an external device via one or more of the second contacts after the connector is coupled to the external device.

2. The catheter of claim 1, wherein the plurality of electrodes is coupled to the plurality of first contacts in a random order that is identified by the pinout map to ensure usability of the catheter.

3. The catheter of claim 1, wherein the plurality of electrodes is coupled to the plurality of first contacts in a non-standard order that is identified by the pinout map to ensure usability of the catheter.

4. The catheter of claim 1, further comprising a plurality of channels, each of the plurality of channels coupled to a respective one of the plurality of electrodes, wherein each of the plurality of electrodes is configured to deliver a signal to a respective one of the plurality of channels.

5. The catheter of claim 4, wherein the pinout map includes a plurality of portions, each portion identifying a different electrode and the respective one of the plurality of channels at which the signal delivered by the electrode is received.

6. The catheter of claim 4, wherein the pinout map includes a plurality of portions, each portion identifying a different electrode and respective first contact which the electrode is coupled to.

7. The catheter of claim 1, wherein the memory is further configured to receive the pinout map via the at least one of the one or more second contacts.

8. The catheter of claim 1, wherein the pinout map includes a plurality of mappings, each mapping identifying a different one of the plurality of electrodes and the first contact the electrode is coupled to.

* * * * *

UNITED STATES PATENT AND TRADEMARK OFFICE
CERTIFICATE OF CORRECTION

PATENT NO. : 11,779,252 B2
APPLICATION NO. : 17/204504
DATED : October 10, 2023
INVENTOR(S) : Eden Kidishman et al.

Page 1 of 1

It is certified that error appears in the above-identified patent and that said Letters Patent is hereby corrected as shown below:

On the Title Page

In Item (*) under "Notice", in Column 1, Line 4, insert -- This patent is subject to a terminal disclaimer --.

In the Specification

In Column 4, Line 27, delete "so and" and insert -- so --, therefor.
In Column 9, Line 63, delete "the end the end" and insert -- the end --, therefor.
In Column 11, Line 41, delete "1310" and insert -- 1310. --, therefor.
In Column 12, Line 15, delete "based" and insert -- based on --, therefor.
In Column 13, Line 43, delete "in the in the" and insert -- in the --, therefor.
In Column 13, Line 53, delete "an a" and insert -- a --, therefor.
In Column 14, Line 29, delete "its each" and insert -- each --, therefor.
In Column 15, Line 51, delete "capable of capable of" and insert -- capable of --, therefor.
In Column 15, Line 58, delete "based" and insert -- based on --, therefor.
In Column 16, Line 59, delete "in the in the" and insert -- in the --, therefor.
In Column 17, Line 32, delete "is" and insert -- is a --, therefor.
In Column 22, Line 20, delete "which in" and insert -- in --, therefor.

Signed and Sealed this
Twenty-seventh Day of February, 2024

Katherine Kelly Vidal
*Director of the United States Patent and Trademark Office*